US008530382B2

(12) United States Patent
Tam

(10) Patent No.: US 8,530,382 B2
(45) Date of Patent: Sep. 10, 2013

(54) ANTHRANILIC DIAMIDE COMPOSITIONS FOR PROPAGULE COATING

(75) Inventor: Wilson Tam, Garnet Valley, PA (US)

(73) Assignee: E I du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 13/392,104

(22) PCT Filed: Sep. 3, 2010

(86) PCT No.: PCT/US2010/047802
§ 371 (c)(1),
(2), (4) Date: Feb. 24, 2012

(87) PCT Pub. No.: WO2011/028996
PCT Pub. Date: Mar. 10, 2011

(65) Prior Publication Data
US 2012/0157305 A1 Jun. 21, 2012

Related U.S. Application Data

(60) Provisional application No. 61/239,909, filed on Sep. 4, 2009.

(51) Int. Cl.
*A01N 25/26* (2006.01)
*A01N 43/60* (2006.01)
*A01N 43/40* (2006.01)
*A61K 31/44* (2006.01)

(52) U.S. Cl.
USPC .......................... 504/100; 504/253; 514/341

(58) Field of Classification Search
None
See application file for complete search history.

(56) References Cited

U.S. PATENT DOCUMENTS

| | | | |
|---|---|---|---|
| 6,747,047 B2 | 6/2004 | Lahm et al. | |
| 7,696,232 B2 * | 4/2010 | Berger et al. | 514/341 |
| 2004/0209923 A1 | 10/2004 | Berger et al. | |
| 2005/0202986 A1 | 9/2005 | Hu et al. | |
| 2007/0259016 A1 | 11/2007 | Hodge et al. | |
| 2008/0103044 A1 | 5/2008 | Tang et al. | |
| 2008/0262061 A1 | 10/2008 | Roberts et al. | |
| 2009/0133318 A1 | 5/2009 | Lahm | |

FOREIGN PATENT DOCUMENTS

| | | |
|---|---|---|
| CN | 101715761 A | 6/2010 |
| EP | 0943241 A1 | 9/1999 |
| JP | 2008150302 A | 3/2008 |
| WO | WO 99/29169 A1 | 6/1999 |
| WO | WO 03/015519 A1 | 2/2003 |
| WO | WO 03/024222 A1 | 3/2003 |
| WO | WO 2004/067528 A1 | 8/2004 |
| WO | WO 2005/089546 A1 | 9/2005 |
| WO | WO 2006/023783 A1 | 3/2006 |
| WO | WO 2007/003319 A2 | 1/2007 |
| WO | WO 2007/081553 A2 | 7/2007 |
| WO | WO 2007/081965 A2 | 7/2007 |
| WO | WO 2007/081965 A3 | 7/2007 |
| WO | WO 2007/003319 A3 | 11/2007 |
| WO | WO 2008/069990 A1 | 6/2008 |
| WO | WO 2008/107097 A1 | 9/2008 |
| WO | WO 2009/002856 A1 | 12/2008 |
| WO | WO 2009/113712 A2 | 9/2009 |
| WO | WO 2011/028993 A1 | 3/2011 |
| WO | WO-2011049233 * | 4/2011 |

OTHER PUBLICATIONS

X. Guo et al., "Calculation of hydrophile—lipophile balance . . . ", *Journal of Colloid and Interface Science* 2006, 298, 441-450.
"What is Horticultural Oil and Dormant Oil?" published in *Weekend Gardener Monthly Web Magazine*, Jun. 2009 (available Jun. 30, 2009 from http://www.weekendgarder.net/garden-pests/dormantoil-010901.htm).
Technical Bulletin "Pluronic® L35 Block Copolymer Surfactant", 2004, BASF, Florham Park, New Jersey.
É. Kiss et al., "Adsorption and Wetting Properties . . . ", *Journal of Adhesion* 2004, 80, 815-829.

* cited by examiner

*Primary Examiner* — Alton Pryor
(74) *Attorney, Agent, or Firm* — Craig L. Hillemann

(57) ABSTRACT

Disclosed is an insecticidal composition comprising by weight based on the total weight of the composition:
(a) from about 9 to about 91% of one or more anthranilic diamide insecticides; and
(b) from about 9 to about 91% of a nonionic ethylene oxide-propylene oxide block copolymer component having a water solubility of at least about 5% by weight at 20° C., a hydrophilic-lipophilic balance value of at least about 5 and an average molecular weight ranging from about 1500 to about 20000 daltons;
wherein the ratio of component (b) to component (a) is about 1:10 to about 10:1 by weight.
Also disclosed is a geotropic propagule coated with an insecticidally effective amount of the aforedescribed composition. Further disclosed is a liquid composition consisting of about 5 to 80 weight % of the aforedescribed composition and about 20 to 95 weight % of a volatile aqueous liquid carrier, and a method for protecting a geotropic propagule and plant derived therefrom from a phytophagous insect pest, the method comprising coating the propagule with an insecticidally effective amount of the aforedescribed liquid composition and then evaporating the volatile aqueous liquid carrier.

15 Claims, No Drawings

US 8,530,382 B2

ANTHRANILIC DIAMIDE COMPOSITIONS FOR PROPAGULE COATING

FIELD OF THE INVENTION

This invention relates to compositions comprising anthranilic diamide insecticides and nonionic ethylene oxide-propylene oxide block copolymers. This invention also relates to geotropic propagules coated with these compositions and to protecting propagules and derived plants from phytophagous insect pests by contacting the propagules with these compositions.

BACKGROUND OF THE INVENTION

Damage by phytophagous insect pests to geotropic propagules such as seeds, rhizomes, tubers, bulbs or corms, and plants derived therefrom causes significant economic losses.

Anthranilic diamides, alternatively called anthranilamides, are a recently discovered class of insecticides having activity against numerous insect pests of economic importance. PCT Publication WO 03/024222 discloses treatment with anthranilic diamides being useful for protecting propagules from phytophagous invertebrate pests. Furthermore, because of the ability of anthranilic diamides to translocate within plants, not only the propagules, but also new growth developing from the propagules can be protected.

Although anthranilic diamides have properties making them suitable for protecting propagules and developing growth, achieving sufficient absorption of anthranilic diamides into the propagule and developing roots to cause insecticidally effective concentrations in parts of the developing plant for which protection is desired can be problematical. Although anthranilic diamide coatings on propagules are exposed to moisture from the propagules and surrounding plant growing medium (e.g., soil), the low water solubility of anthranilic diamide insecticides impedes their mobilization through moisture. Also, until the anthranilic diamides are absorbed into the propagules and developing roots, they are vulnerable to absorption and dissipation through the growing medium.

Achieving insecticidally effective concentrations of anthranilic diamides in foliage by treating propagules requires greater amounts of anthranilic diamides to be available for transport as distances within the plant increase. Because the rapidly expanding volume of plant tissue in growing foliage inherently dilutes anthranilic diamide concentrations, absorption of increased amounts of anthranilic diamides is required for protection of foliage, particularly if protection of foliage beyond the first couple leaves and during a substantial part of the growing season is desired.

Accordingly, need exists for new compositions promoting the absorption of anthranilic diamide insecticides into propagules and developing roots. Such compositions have now been discovered.

SUMMARY OF THE INVENTION

One aspect of the present invention is an insecticidal composition comprising by weight based on the total weight of the composition:
(a) from about 9 to about 91% of one or more anthranilic diamide insecticides; and
(b) from about 9 to about 91% of a nonionic ethylene oxide-propylene oxide block copolymer component having a water solubility of at least about 5% by weight at 20° C., a hydrophilic-lipophilic balance value of at least about 5 and an average molecular weight ranging from about 1500 to about 20000 daltons;
wherein the ratio of component (b) to component (a) is about 1:10 to about 10:1 by weight.

Another aspect of the present invention is a geotropic propagule coated with an insecticidally effective amount of the aforedescribed composition.

Another aspect of the present invention is a liquid composition consisting of about 5 to 80 weight % of the aforedescribed composition and about 20 to 95 weight % of a volatile aqueous liquid carrier.

Another aspect of the present invention is a method for protecting a geotropic propagule and plant derived therefrom from a phytophagous insect pest, the method comprising coating the propagule with an insecticidally effective amount of the aforedescribed liquid composition and then evaporating the volatile aqueous liquid carrier of the composition.

DETAILS OF THE INVENTION

As used herein, the terms "comprises," "comprising," "includes," "including," "has," "having," "contains", "containing," "characterized by" or any other variation thereof, are intended to cover a non-exclusive inclusion, subject to any limitation explicitly indicated. For example, a composition, mixture, process or method that comprises a list of elements is not necessarily limited to only those elements but may include other elements not expressly listed or inherent to such composition, mixture, process or method.

The transitional phrase "consisting of" generally excludes any element, step, or ingredient not specified. If in a claim, "consisting of" would close the claim to the inclusion of materials other than those recited except for impurities ordinarily associated therewith. However, when the phrase "consisting of" appears immediately after the preamble in a composition claim including a component (e.g., ingredient) itself defined using the word "comprising", then said component can also include constituents not expressly listed, subject to the limitation that the total amount of all constituents in said component must be within any delimiting amounts stated for said component in the composition. Furthermore, when the phrase "consisting of" appears in a clause of the body of a claim, rather than immediately following the preamble, it limits only the element set forth in that clause; other elements are not excluded from the claim as a whole.

The transitional phrase "consisting essentially of" is used to define a composition, or method that includes materials, steps, features, components, or elements, in addition to those literally disclosed, provided that these additional materials, steps, features, components, or elements do not materially affect the basic and novel characteristic(s) of the claimed invention. The term "consisting essentially of" occupies a middle ground between "comprising" and "consisting of".

Where applicants have defined an invention or a portion thereof with an open-ended term such as "comprising," it should be readily understood that (unless otherwise stated) the description should be interpreted to also describe such an invention using the terms "consisting essentially of" or "consisting of."

Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

As referred to in the present disclosure and claims, the term "propagule" means a seed or a regenerable plant part. The term "regenerable plant part" means a part of a plant other than a seed from which a whole plant may be grown or regenerated when the plant part is placed in horticultural or agricultural growing media such as moistened soil, peat moss, sand, vermiculite, perlite, rock wool, fiberglass, coconut husk fiber, tree fern fiber and the like, or even a completely liquid medium such as water. The term "geotropic propagule" means a seed or a regenerable plant part obtained from the portion of a plant ordinarily disposed below the surface of the growing medium. Geotropic regenerable plant parts include viable divisions of rhizomes, tubers, bulbs and corms which retain meristematic tissue, such as an eye. Regenerable plant parts such as cut or separated stems and leaves derived from the foliage of a plant are not geotropic and thus are not considered geotropic propagules. As referred to in the present disclosure and claims, unless otherwise indicated, the term "seed" specifically refers to an unsprouted seed or seeds. The term "foliage" refers to parts of a plant exposed above ground. Therefore foliage includes leaves, stems, branches, flowers, fruits and buds.

In the context of the present disclosure and claims, protection of a seed or plant grown therefrom from a phytophagous insect pest means protection of the seed or plant from injury or damage potentially caused by the insect pest. This protection is achieved through control of the insect pest. Control of an insect pest can include killing the insect pest, interfering with its growth, development or reproduction, and/or inhibiting its feeding. In the present disclosure and claims the terms "insecticidal" and "insecticidally" relate to any form of insect control.

The terms "suspension concentrate" and "suspension concentrate composition" refer to compositions comprising finely divided solid particles of an active ingredient dispersed in a continuous liquid phase. Said particles retain identity and can be physically separated from the continuous liquid phase. The viscosity of the continuous liquid phase can vary from low to high, and indeed can be so high as to cause the suspension concentrate composition to have a gel-like or paste-like consistency.

The term "particle size" refers to the equivalent spherical diameter of a particle, i.e., the diameter of a sphere enclosing the same volume as the particle. "Median particle size" is the particle size corresponding to half of the particles being larger than the median particle size and half being smaller. With reference to particle size distribution, percentages of particles are also on a volume basis (e.g., "at least 95% of the particles are less than about 10 microns" means that at least 95% of the aggregate volume of particles consists of particles having equivalent spherical diameters of less than about 10 microns). The principles of particle size analysis are well known to those skilled in the art; for a technical paper providing a summary, see A. Rawle, "Basic Principles of Particle Size Analysis" (document MRK034 published by Malvern Instruments Ltd., Malvern, Worcestershire, UK). Volume distributions of particles in powders can be conveniently measured by such techniques as Low Angle Laser Light Scattering (also known as LALLS and Laser Diffraction), which relies on the fact that diffraction angle is inversely proportional to particle size.

In the recitations herein, the term "alkyl" used either alone or in compound words such as "haloalkyl" or "fluoroalkyl" includes straight-chain or branched alkyl, such as methyl, ethyl, n-propyl, i-propyl, or the different butyl isomers. "Alkoxy" includes, for example, methoxy, ethoxy, n-propyloxy, isopropyloxy and the different butoxy isomers. The term "halogen", either alone or in compound words such as "haloalkyl", includes fluorine, chlorine, bromine or iodine. Further, when used in compound words such as "haloalkyl" or "haloalkoxy", said alkyl may be partially or fully substituted with halogen atoms which may be the same or different. Examples of "haloalkyl" include $CF_3$, $CH_2Cl$, $CH_2CF_3$ and $CCl_2CF_3$. The terms "haloalkoxy", and the like, are defined analogously to the term "haloalkyl". Examples of "haloalkoxy" include $OCF_3$, $OCH_2Cl_3$, $OCH_2CH_2CHF_2$ and $OCH_2CF_3$.

The total number of carbon atoms in a substituent group is indicated by the "$C_i$-$C_j$" prefix where i and j are numbers from 1 to 4. For example, $C_1$-$C_4$ alkyl designates methyl through butyl, including the various isomers.

In the present disclosure and claims, "EO/PO" is an abbreviation for "ethylene oxide-propylene oxide". In percentage ranges, if the percent sign "%" is shown after only the second number delimiting a range, it refers to both numbers delimiting the range. For example, "from about 9 to about 91%" means "from about 9% to about 91%".

Embodiments of the present invention include:

Embodiment 1

The insecticidal composition described in the Summary of the Invention comprising by weight based on the total weight of the composition:
(a) from about 9 to about 91% of one or more anthranilic diamide insecticides; and
(b) from about 9 to about 91% of a nonionic ethylene oxide-propylene oxide (EO/PO) block copolymer component having a water solubility of at least about 5% by weight at 20° C., a hydrophilic-lipophilic balance value of at least about 5 and an average molecular weight ranging from about 1500 to about 20000 daltons;
wherein the ratio of component (b) to component (a) is about 1:10 to about 10:1 by weight.

Embodiment 2

The composition of Embodiment 1 wherein component (a) (i.e. one or more anthranilic diamide insecticides) comprises at least one compound selected from anthranilic diamides of Formula 1, N-oxides, and salts thereof,

1 wherein
X is N, CF, CCl, CBr or Cl;
$R^1$ is $CH_3$, Cl, Br or F;
$R^2$ is H, F, Cl, Br or —CN;
$R^3$ is F, Cl, Br, $C_1$-$C_4$ haloalkyl or $C_1$-$C_4$ haloalkoxy;
$R^{4a}$ is H, $C_1$-$C_4$ alkyl, cyclopropylmethyl or 1-cyclopropylethyl;
$R^{4b}$ is H or $CH_3$;
$R^5$ is H, F, Cl or Br; and
$R^6$ is H, F, Cl or Br.

Embodiment 3

The composition of Embodiment 2 wherein component (a) is selected from anthranilic diamides of Formula 1, N-oxides, and salts thereof.

Embodiment 3a

The composition of Embodiment 3 wherein component (a) is selected from anthranilic diamides of Formula 1 and salts thereof.

Embodiment 4

The composition of Embodiment 3a wherein component (a) is selected from anthranilic diamides of Formula 1.

Embodiment 5

The composition of any one of Embodiments 2 through 4 wherein X is N; $R^1$ is $CH_3$; $R^2$ is Cl or —CN; $R^3$ is Cl, Br or $CF_3$; $R^{4a}$ is $C_1$-$C_4$ alkyl; $R^{4b}$ is H; $R^5$ is Cl; and $R^6$ is H.

Embodiment 6

The composition of Embodiment 5 wherein $R^{4a}$ is $CH_3$ or $CH(CH_3)_2$.

Embodiment 7

The composition of Embodiment 6 wherein $R^3$ is Br; and $R^{4a}$ is $CH_3$ (i.e. the compound of Formula 1 is chlorantraniliprole or cyantraniliprole, or optionally an N-oxide or salt thereof).

Embodiment 7a

The (insecticidal) composition described in the Summary of the Invention or Embodiment 1 wherein component (a) (i.e. the one or more anthranilic diamide insecticides) comprises chlorantraniliprole, cyantraniliprole or a mixture thereof.

Embodiment 8

The composition of Embodiment 7 wherein $R^2$ is Cl (i.e. the compound of Formula 1 is chlorantraniliprole, or optionally an N-oxide or salt thereof).

Embodiment 8a

The (insecticidal) composition described in the Summary of the Invention or Embodiment 1 wherein component (a) comprises chlorantraniliprole.

Embodiment 9

The composition of Embodiment 7 wherein $R^2$ is —CN (i.e. the compound of Formula 1 is cyantraniliprole, or optionally an N-oxide or salt thereof).

Embodiment 9a

The (insecticidal) composition described in the Summary of the Invention or Embodiment 1 wherein component (a) comprises cyantraniliprole.

Embodiment 10

The composition of any one of Embodiments 1 through 9a wherein component (a) is at least about 10% of the composition by weight.

Embodiment 11

The composition of Embodiment 10 wherein component (a) is at least about 20% of the composition by weight.

Embodiment 12

The composition of Embodiment 11 wherein component (a) is at least about 30% of the composition by weight.

Embodiment 13

The composition of Embodiment 12 wherein component (a) is at least about 40% of the composition by weight.

Embodiment 14

The composition of any one of Embodiments 1 through 13 wherein component (a) is not more than about 90% of the composition by weight.

Embodiment 15

The composition of Embodiment 14 wherein component (a) is not more than about 80% of the composition by weight.

Embodiment 16

The composition of Embodiment 15 wherein component (a) is not more than about 70% of the composition by weight.

Embodiment 17

The composition of any one of Embodiments 1 through 16 wherein not more than about 30% of component (a) is present in the composition as solid particles having a particle size greater than about 10 μm.

Embodiment 18

The composition of Embodiment 17 wherein not more than about 20% of component (a) is present in the composition as solid particles having a particle size greater than about 10 μm.

Embodiment 19

The composition of Embodiment 18 wherein not more than about 10% of component (a) is present in the composition as solid particles having a particle size greater than about 10 μm.

Embodiment 20

The composition of any one of Embodiments 1 through 19 wherein component (b) (i.e. the nonionic ethylene oxide-propylene oxide (EO/PO) block copolymer component) has a water solubility of at least about 10% at 20° C.

Embodiment 21

The composition of Embodiment 20 wherein component (b) has a water solubility of at least about 25% at 20° C.

Embodiment 22

The composition of any one of Embodiments 1 through 21 wherein component (b) has a hydrophilic-lipophilic balance (HLB) value of at least about 6.

Embodiment 23

The composition of Embodiment 22 wherein component (b) has an HLB value of at least about 7.

Embodiment 24

The composition of Embodiment 23 wherein component (b) has an HLB value of at least about 8.

Embodiment 25

The composition of Embodiment 24 wherein component (b) has an HLB value of at least about 10.

Embodiment 26

The composition of Embodiment 25 wherein component (b) has an HLB value of at least about 20.

Embodiment 27

The composition of Embodiment 26 wherein component (b) has an HLB value of at least about 22.

Embodiment 28

The composition of any one of Embodiments 1 through 27 wherein component (b) has an HLB value of not more than about 40.

Embodiment 29

The composition of Embodiment 28 wherein component (b) has an HLB value of not more than about 35.

Embodiment 30

The composition of Embodiment 29 wherein component (b) has an HLB value of not more than about 31.

Embodiment 31

The composition of any one of Embodiments 1 through 26 wherein component (b) has an HLB value of not more than about 20.

Embodiment 32

The composition of any one of Embodiments 1 through 25 wherein component (b) has an HLB value of not more than about 15.

Embodiment 33

The composition of any one of Embodiments 1 through 32 wherein component (b) (separate from the composition) is a paste or solid at 20° C.

Embodiment 34

The composition of any one of Embodiments 1 through 31 wherein component (b) (separate from the composition) is a solid at 20° C.

Embodiment 35

The composition of any one of Embodiments 1 through 34 wherein component (b) has an average molecular weight of at least about 3000 daltons.

Embodiment 36

The composition of Embodiment 35 wherein component (b) has an average molecular weight of at least about 5000 daltons.

Embodiment 37

The composition of Embodiment 36 wherein component (b) has an average molecular weight of at least about 10000 daltons.

Embodiment 38

The composition of Embodiment 37 wherein component (b) has an average molecular weight of at least about 15000 daltons.

Embodiment 39

The composition of any one of Embodiments 1 through 37 wherein component (b) has an average molecular weight of not more than about 10000 daltons.

Embodiment 40

The composition of Embodiment 36 wherein component (b) has an average molecular weight of not more than about 7000 daltons.

Embodiment 41

The composition of any one of Embodiments 1 through 40 wherein component (b) (i.e. the nonionic EO/PO block copolymer component) is at least about 10% of the composition by weight.

Embodiment 42

The composition of Embodiment 41 wherein component (b) is at least about 15% of the composition by weight.

Embodiment 43

The composition of Embodiment 42 wherein component (b) is at least about 20% of the composition by weight.

Embodiment 44

The composition of Embodiment 43 wherein component (b) is at least about 25% of the composition by weight.

Embodiment 45

The composition of Embodiment 44 wherein component (b) is at least about 30% of the composition by weight.

Embodiment 46

The composition of Embodiment 45 wherein component (b) is at least about 35% of the composition by weight.

Embodiment 47

The composition of Embodiment 46 wherein component (b) is at least about 40% of the composition by weight.

Embodiment 48

The composition of any one of Embodiments 1 through 47 wherein component (b) is not more than about 80% of the composition by weight.

Embodiment 49

The composition of Embodiment 48 wherein component (b) is not more than about 70% of the composition by weight.

Embodiment 50

The composition of Embodiment 49 wherein component (b) is not more than about 60% of the composition by weight.

Embodiment 51

The composition of Embodiment 50 wherein component (b) is not more than about 50% of the composition by weight.

Embodiment 52

The composition of Embodiment 51 wherein component (b) is not more than about 40% of the composition by weight.

Embodiment 53

The composition of any one of Embodiments 1 through 52 wherein the ratio of component (b) to component (a) is at least about 1:8 (by weight).

Embodiment 54

The composition of Embodiment 53 wherein the ratio of component (b) to component (a) is at least about 1:5.

Embodiment 55

The composition of Embodiment 54 wherein the ratio of component (b) to component (a) is at least about 1:4.

Embodiment 56

The composition of Embodiment 55 wherein the ratio of component (b) to component (a) is at least about 1:3.

Embodiment 57

The composition of Embodiment 56 wherein the ratio of component (b) to component (a) is at least about 1:2.

Embodiment 58

The composition of Embodiment 57 wherein the ratio of component (b) to component (a) is at least about 1:1.

Embodiment 59

The composition of Embodiment 58 wherein the ratio of component (b) to component (a) is at least about 2:1.

Embodiment 60

The composition of Embodiment 59 wherein the ratio of component (b) to component (a) is at least about 3:1.

Embodiment 61

The composition of Embodiment 60 wherein the ratio of component (b) to component (a) is at least about 4:1.

Embodiment 61a. The composition of Embodiment 61 wherein the ratio of component (b) to component (a) is at least about 5:1.

Embodiment 62

The composition of Embodiment 61a wherein the ratio of component (b) to component (a) is at least about 8:1.

Embodiment 63

The composition of any one of Embodiments 1 through 58 wherein the ratio of component (b) to component (a) is not more than about 1:1.

Embodiment 64

The (insecticidal) composition described in the Summary of the Invention or any one of Embodiments 1 through 63 wherein component (b) comprises one or more nonionic EO/PO block copolymers selected from the group consisting of poloxamers, reverse poloxamers, poloxamines and reverse poloxamines.

Embodiment 65

The composition of Embodiment 64 wherein component (b) comprises one or more nonionic EO/PO block copolymers selected from the group consisting of poloxamers and poloxamines.

Embodiment 66

The composition of Embodiment 64 wherein component (b) comprises one or more nonionic EO/PO block copolymers selected from the group consisting of poloxamers and reverse poloxamers.

Embodiment 67

The composition of any one of Embodiments 64 through 66 wherein component (b) comprises one or more nonionic EO/PO block copolymers selected from poloxamers.

Embodiment 68

The composition of Embodiment 67 wherein component (b) consists essentially of one or more poloxamers.

Embodiment 69

The composition of Embodiment 67 or 68 wherein the poloxamers have a polyoxypropylene chain with an average molecular weight of at least about 900 daltons.

Embodiment 70

The composition of Embodiment 69 wherein the polyoxypropylene chain has an average molecular weight of at least about 1200 daltons.

Embodiment 71

The composition of Embodiment 70 wherein the polyoxypropylene chain has an average molecular weight of at least about 1700 daltons.

Embodiment 72

The composition of Embodiment 71 wherein the polyoxypropylene chain has an average molecular weight of at least about 2000 daltons.

Embodiment 73

The composition of any one of Embodiments 67 through 72 wherein the poloxamers have a polyoxypropylene chain with an average molecular weight of not more than about 4000 daltons.

Embodiment 74

The composition of Embodiment 73 wherein the polyoxypropylene chain has an average molecular weight of not more than about 3000 daltons.

Embodiment 75

The composition of Embodiment 74 wherein the polyoxypropylene chain has an average molecular weight of not more than about 2000 daltons.

Embodiment 76

The composition of any one of Embodiments 64 through 75 wherein the poloxamers, poloxamines, reverse poloxamers and reverse poloxamines have a polyoxyethylene content of at least about 20% by weight.

Embodiment 77

The composition of Embodiment 76 wherein the polyoxyethylene content is at least about 30% by weight.

Embodiment 78

The composition of Embodiment 77 wherein the polyoxyethylene content is at least about 40% by weight.

Embodiment 79

The composition of Embodiment 78 wherein the polyoxyethylene content is at least about 50% by weight.

Embodiment 80

The composition of Embodiment 79 wherein the polyoxyethylene content is at least about 60% by weight.

Embodiment 81

The composition of Embodiment 80 wherein the polyoxyethylene content is at least about 70% by weight.

Embodiment 82

The composition of any one of Embodiments 64 through 81 wherein the poloxamers, poloxamines, reverse poloxamers and reverse poloxamines have a polyoxyethylene content of not more than about 90% by weight.

Embodiment 83

The composition of Embodiment 82 wherein the polyoxyethylene content is not more than about 80% by weight.

Embodiment 84

The composition of any one of Embodiments 1 through 83 further comprising (c) up to about 82% by weight of one or more biologically active agents other than anthranilic diamide insecticides.

Embodiment 85

The composition of Embodiment 84 wherein component (c) (i.e. the one or more biologically active agents other than anthranilic diamide insecticides) is at least 0.1% of the composition by weight.

Embodiment 86

The composition of Embodiment 85 wherein component (c) is at least 1% of the composition by weight.

Embodiment 87

The composition of any one of Embodiments 84 through 86 wherein component (c) is not more than about 60% of the composition by weight.

Embodiment 88

The composition of Embodiment 87 wherein component (c) is not more than about 20% of the composition by weight.

Embodiment 89

The composition of any one of Embodiments 84 through 88 wherein component (c) comprises at least one fungicide or insecticide (other than anthranilic diamide insecticides).

Embodiment 90

The composition of Embodiment 89 wherein component (c) comprises at least one insecticide.

Embodiment 91

The composition of Embodiment 89 or 90 wherein component (c) comprises at least one fungicide.

Embodiment 91a

The composition of any one of Embodiments 1 through 83 wherein the composition does not comprise a biologically active agent other than component (a).

Embodiment 92

The composition of any one of Embodiments 1 through 91a wherein the composition further comprises (d) up to about 80% by weight of one or more inert formulating ingredients other than nonionic EO/PO block copolymers.

Embodiment 93

The composition of Embodiment 92 wherein component (d) (i.e. the one or more inert formulating ingredients other than nonionic EO/PO block copolymers) is at least about 0.01% of the composition by weight.

Embodiment 93a

The composition of Embodiment 93 wherein component (d) is at least about 0.1% of the composition by weight.

Embodiment 94

The composition of any one of Embodiments 92 through 93a wherein component (d) is not more than about 20% of the composition by weight.

Embodiment 95

The composition of any one of Embodiments 92 through 94 wherein component (d) comprises at least one inert formulating ingredient selected from the group consisting of adhesives, liquid diluents, solid diluents, surfactants, antifreeze agents, preservatives, thickening agents and fertilizers.

Embodiment 96

The geotropic propagule described in the Summary of the Invention which is coated with an insecticidally effective amount of the composition of any one of Embodiments 1 through 95.

Embodiment 97

The geotropic propagule of Embodiment 96 which is a seed.

Embodiment 98

The seed of Embodiment 97 which is a seed of cotton, maize, soybean, rapeseed or rice.

Embodiment 99

The seed of Embodiment 98 which is a seed of maize or rapeseed.

Embodiment 100

The seed of Embodiment 99 which is a seed of maize.

Embodiment 101

The seed of Embodiment 99 which is a seed of rapeseed.

Embodiment 102

The liquid composition described in the Summary of the Invention consisting of about 5 to 80 weight % of the composition of any one of Embodiments 1 through 95 and about 20 to 95 weight % of a volatile aqueous liquid carrier.

Embodiment 103

The liquid composition of Embodiment 102 wherein the volatile aqueous liquid carrier is at least about 25% of the (liquid) composition by weight.

Embodiment 104

The liquid composition of Embodiment 103 wherein the volatile aqueous liquid carrier is at least about 30% of the (liquid) composition by weight.

Embodiment 105

The liquid composition of any one of Embodiments 102 through 104 wherein the volatile aqueous liquid carrier is not more than about 70% of the (liquid) composition by weight.

Embodiment 106

The liquid composition of any one of Embodiments 102 through 105 wherein the volatile aqueous liquid carrier comprises at least about 80% water by weight.

Embodiment 107

The liquid composition of Embodiment 106 wherein the volatile aqueous liquid carrier comprises at least about 90% water by weight.

Embodiment 108

The liquid composition of Embodiment 107 wherein the volatile aqueous liquid carrier comprises at least about 95% water by weight.

Embodiment 109

The liquid composition of Embodiment 108 wherein the volatile aqueous liquid carrier consists essentially of water.

Embodiment 110

The liquid composition of Embodiment 109 wherein the volatile aqueous liquid carrier is water.

Embodiment 111

The liquid composition of any one of Embodiments 102 through 110 wherein at least some of component (a) is present in the liquid composition as solid particles.

Embodiment 112

The liquid composition of Embodiment 111 wherein at least about 90% of component (a) is present in the composition as solid particles.

Embodiment 113

The liquid composition of Embodiment 112 wherein at least about 95% of component (a) is present in the composition as solid particles.

Embodiment 114

The liquid composition of Embodiment 113 wherein at least about 98% of component (a) is present in the composition as solid particles.

Embodiment 115

The liquid composition of any one of Embodiments 111 through 114 wherein more than 95% by weight of the particles have a particle size less than about 10 μm.

Embodiment 116

The liquid composition of any one of Embodiments 111 through 115 wherein the median particle size of the particles is not more than about 10 μm.

Embodiment 117

The liquid composition of Embodiment 115 or 116 wherein the median particle size of the particles is not more than about 4 μm.

Embodiment 118

The liquid composition of Embodiment 117 wherein the median particle size of the particles is not more than about 3 μm.

Embodiment 119

The liquid composition of Embodiment 118 wherein the median particle size of the particles in not more than about 2 μm.

Embodiment 120

The liquid composition of Embodiment 119 wherein the median particle size of the particles is not more than about 1 μm.

Embodiment 121

The liquid composition of any one of Embodiments 111 through 120 wherein the median particle size of the particles is at least about 0.1 μm.

Embodiment 122

The method described in the Summary of the Invention for protecting a geotropic propagule and plant derived therefrom from a phytophagous insect pest, the method comprising coating the propagule with an insecticidally effective amount of the liquid composition of any one of Embodiments 102 through 121 and then evaporating the volatile aqueous liquid carrier.

Embodiment 123

The method of Embodiment 122 wherein the insect pest is in a taxonomic order selected from Hemiptera and Lepidoptera.

Embodiment 124

The method of Embodiment 123 wherein the insect pest is in a taxonomic family selected from Aleyrodidae, Aphidadae, Cicadellidae, Delphacidae, Gelechiidae, Lymantriidae, Noctuidae, Plutellidae, Pyralidae and Torticidae.

Embodiment 125

The method of Embodiment 124 wherein the insect pest is in the family Noctuidae.

Embodiment 126

The method of any one of Embodiments 122 through 125 wherein the geotropic propagule is a seed.

Embodiment 127

The method of Embodiment 126 wherein the seed is a seed of cotton, maize, soybean, rapeseed or rice.

Embodiment 128

The method of Embodiment 127 wherein the seed is a seed of maize or rapeseed.

Embodiment 129

The method of Embodiment 128 wherein the seed of maize.

Embodiment 130

The method of Embodiment 128 wherein the seed is a seed of rapeseed.

Embodiments of this invention can be combined in any manner. An example of such combination is the insecticidal composition described in the Summary of the Invention comprising by weight (a) from about 9 to about 91% of one or more anthranilic diamide insecticides; and (b) from about 9 to about 91% of a nonionic EO/PO block copolymer component having a water solubility of at least about 5% by weight at 20° C., an HLB value ranging from about 5 to about 31 and an average molecular weight ranging from about 3000 to about 15000 daltons; wherein the ratio of component (b) to component (a) is about 1:5 to about 5:1 by weight.

The present invention relates to the protection of a geotropic propagule and plant derived therefrom from a phytophagous insect pest by coating the propagule with an insecticidally effective amount of an insecticidal composition comprising by weight based on the total weight of the composition:
- (a) from about 9 to about 91% of one or more anthranilic diamide insecticides; and
- (b) from about 9 to about 91% of a nonionic ethylene oxide-propylene oxide block copolymer component having a water solubility of at least about 5% by weight at 20° C., a hydrophilic-lipophilic balance value of at least about 5 and an average molecular weight ranging from about 1500 to about 20000 daltons;

wherein the ratio of component (b) to component (a) is about 1:10 to about 10:1 by weight.

The inclusion of nonionic ethylene oxide-propylene oxide block copolymers in the coating composition according to the present invention has been discovered to remarkably facilitate absorption of insecticidal anthranilic diamides into geotropic propagules (e.g., seeds) and/or roots developing from the propagules (e.g., germinating seeds) to enable distribution of insecticidally effective concentrations of the anthranilic diamides in not only the propagules and derived geotropic plant parts but also foliage developing from the propagules.

Anthranilic diamide insecticides, also known as anthranilamide insecticides, are members of a class of insecticidal compounds characterized chemically by molecular structures comprising vicinal carboxamide substituents bonded to the carbon atoms of an aryl ring, typically phenyl, wherein one carboxamide moiety is bonded through the carbonyl carbon and the other carboxamide moiety is bonded through the nitrogen atom and characterized biologically by binding to ryanodine receptors in insect muscle cells, causing the channel to open and release calcium ions into the cytoplasm. Depletion of calcium ion stores results in insect paralysis and death. PCT Publication WO 2004/027042 describes an assay for ryanodine receptor ligands. Illustrative of anthranilic diamide insecticides are compounds of Formula 1, N-oxides, and salts thereof, described in Embodiment 2. A variety of anthranilic diamide insecticides and methods for their preparation are described in the literature. For example, compounds of Formula 1 and methods for their preparation are reported in U.S. Pat. Nos. 6,747,047 and 7,247,647, and PCT Publications WO 2003/015518, WO 2003/015519, WO 2004/067528, WO 2006/062978 and WO 2008/069990.

Of particular note for the present compositions and methods of their use are compounds of Formula 1 wherein X is N; $R^1$ is $CH_3$; $R^2$ is Cl or —CN; $R^3$ is Br; $R^{4a}$ is $CH_3$; $R^{4b}$ is H; $R^5$ is Cl; and $R^6$ is H. The compound wherein $R^2$ is Cl has the Chemical Abstracts systematic name 3-bromo-N-[4-chloro-2-methyl-6-[(methylamino)carbonyl]phenyl]-1-(3-chloro-2-pyridinyl)-1H-pyrazole-5-carboxamide and the common name chlorantraniliprole, and is trademarked as an insecticidal active ingredient by DuPont as RYNAXYPYR. The compound wherein $R^2$ is —CN has the Chemical Abstracts systematic name 3-bromo-1-(3-chloro-2-pyridinyl)-N-[4-cyano-2-methyl-6-[(methylamino)carbonyl]-phenyl]-1H-pyrazole-5-carboxamide and the proposed common name cyantraniliprole, and is trademarked as an insecticidal active ingredient by DuPont as CYAZYPYR. As disclosed in Example 15 of WO 2006/062978, cyantraniliprole is in the form of solids melting at 177-181° C. or 217-219° C., i.e. two different polymorphs. Both polymorphs are suitable for the present compositions and methods.

Most generally, component (a) is from about 9 to about 91% of the composition by weight. Typically component (a) is at least about 20%, more typically at least about 30%, and most typically at least 40% of the composition by weight. Component (a) is typically not more than about 80% and more typically not more than about 70% of the composition by weight. To provide optimal biological availability, typically not more than about 30% of component (a), more typically not more than about 20%, and most typically not more than about 10% of component (a) by weight is present in the composition as particles having a particle size greater than about 10 μm. Particle sizes of 10 μm or less can be easily achieved through such techniques as milling.

The present composition contains as component (b) a nonionic ethylene oxide-propylene oxide (EO/PO) block copolymer component having a water solubility of at least about 5% at 20° C., a hydrophilic-lipophilic balance (HLB) value of at least about 5 and an average molecular weight ranging from about 1500 to about 20000 daltons. This component consists essentially of one or more nonionic ethylene oxide-propylene oxide block copolymers. The inclusion in the composition of present invention of at least about 9% by weight and in a ratio of at least about 1:10 relative to component (a) of a nonionic EO/PO block copolymer having the above described water solubility, HLB value and average molecular weight has been discovered when the composition is coated on a propagule to remarkably promote the absorption of the component (a) active ingredient into the propagule either directly or through the emerging roots, thereby providing more uptake of anthranilic diamide insecticides into the developing plant, including emerging foliage. Increasing uptake of anthranilic diamide insecticides provides insecticidally effective concentrations of the insecticides not only in the propagule, roots and foliage near ground level but also more distant foliage of the growing plant.

Nonionic ethylene oxide-propylene oxide (EO/PO) block copolymers are polymers comprising one or more chains consisting essentially of oxyethylene units ($—OCH_2CH_2—$) units and one or more chains consisting essentially of oxypropylene units ($—OCH(CH_3)CH_2—$). More particularly in the context of the present disclosure and claims, the molecules of nonionic EO/PO block copolymers are considered to consist essentially of polyoxyethylene and polyoxypropylene chains, except that the chains can be connected and/or terminated by other nonionic molecular units, each containing not more than 4 atoms, not counting hydrogen. As the EO/PO block copolymers of component (b) are nonionic, they do not comprise an anionic moiety or a moiety capable of becoming anionic through dissociation (e.g., a carboxylic acid, sulfonic acid, sulfuric acid, phosphonic acid or phosphoric acid functional group, or a salt of one of these acid functional groups). Also, the nonionic EO/PO block copolymers of component (b) do not comprise cationic moieties (e.g., quaternary ammonium salts), but the nonionic EO/PO block copolymers may contain primary, secondary or tertiary amine functionality, subject to the limitation that molecular units other than oxyethylene or oxypropylene units do not contain more than 4 atoms, not counting hydrogen. However, amine functionality is not essential to nonionic EO/PO block copolymers of component (b). Therefore of note is component (b) comprising at least one nonionic EO/PO block copolymer excluding amine functionality. Also of note is component (b) excluding nonionic EO/PO block copolymers containing amine functionality.

Polyoxypropylene chains are lipophilic whereas polyoxyethylene chains are hydrophilic. Combination of a polyoxyethylene chain with a polyoxypropylene chain results in an amphiphilic molecular structure providing surfactant properties. The one or more polyoxyethylene chains in these molecules can be described as the hydrophile, and the one or more polyoxypropylene chains in these molecules can be described as the lipophile. The numbers of oxyethylene and oxypropylene units can be selected to achieve the required physical properties (e.g., water solubility, HLB, molecular weight) for this component.

In the present composition, component (b) (i.e. the nonionic EO/PO block copolymer component) must have a water solubility of at least about 5% by weight at 20° C. Accordingly, component (b) must be soluble in water at 20° C. to the extent of at least about 5% (by weight), which means that a saturated solution or liquid crystalline phase of component (b) in water at 20° C. contains at least about 5% by weight of component (b). (For simplicity, water solubility is accordingly defined in the present disclosure as percent by weight even if "by weight" is not expressly stated.) If component (b) contains multiple nonionic EO/PO block copolymer constituents, typically each constituent has a water solubility of at least about 5% at 20° C. Most nonionic EO/PO block copolymers suitable for component (b) have significantly greater water solubilities (e.g., greater than 10%) and many are miscible with water (e.g., soluble in water in all proportions). Decreased absorption of anthranilic diamide insecticides into a propagule and/or developing roots is observed when water-insoluble PLURONIC L101 or PLURONIC L121 is substituted for a poloxamer having water solubility of at least about 5% as component (b) in a composition coating a seed in soil.

In the context of the present invention, "water solubility" means that component (b) is capable of being completely dissolved in pure water (i.e. the mixtures consist only of water and component (b)) in the weight percentage amount indicated to form (1) a solution consisting of separate EO/PO block copolymer molecules (commonly referred to as unimers) dispersed in the water phase, and/or EO/PO block copolymer molecules aggregated into clusters with hydrophilic components of the molecules forming the exterior and hydrophobic components forming the interior of the clusters (i.e. micelles) randomly dispersed in the water phase, and/or (2) a lyotropic liquid crystalline phase containing clusters of EO/PO block copolymer molecules aggregated so that hydrophilic components of the molecules form the cluster exterior and hydrophobic components form the cluster interior wherein the clusters are isotropically or anisotropically ordered relative to one another in regards to position and/or orientation in the presence of water. Liquid crystalline phases are often viscous or even gel-like, but nevertheless clear. Anisotropic liquid crystalline phases are generally birefringent, whereas isotropic liquid crystalline phases are not. Liquid crystalline phases of certain EO/PO block copolymers are described in P. Alexandridis et al., *Langmuir* 1996, 12, 2690-2700 and P. Alexandridis, *Macromolecules* 1998, 31, 6935-6942. Although a dispersion of micelles in an aqueous medium is a manifestation of water solubility, dispersions and emulsions of droplets (such as of oils and other water-immiscible liquids) lacking both the exterior and interior order of micelles are not examples of water solubility. Microemulsions of droplets differing from micelles by having interiors consisting of constituents besides the hydrophobic components of EO/PO block copolymer molecules are not examples of solutions or water solubility according to the present definition. For further reference to solubility of EO/PO block copolymers, see Section 4.1 "Surfactant Solubility" in Drew Myers, *Surfactant Science and Technology, Third Edition*, John Wiley, 2005.

The inclusion of polyoxyethylene and polyoxypropylene chains provides nonionic EO/PO block copolymer molecules with an amphiphilic combination of well-defined hydrophilic and lipophilic regions, thereby resulting in ability to function as a surfactant. The hydrophilic-lipophilic balance (HLB) of a surfactant is an overall measure of the degree to which it is hydrophilic or lipophilic, and is determined by the ratio of polar and non-polar groups in the surfactant molecule. The HLB value (i.e. number) of a surfactant indicates the polarity of the surfactant molecules in an arbitrary range of 1 to 40, wherein the number increases with increasing hydrophilicity. The HLB value for a surfactant can be determined by the "emulsion comparison method" of Griffin (W. C. Griffin, *J. Soc. Cosmet. Chem.* 1949, 1, 311-326). Alternatively, the HLB value can be estimated numerically or predicted by a variety of experimental techniques; see X. Guo et al., *Journal of Colloid and Interface Science* 2006, 298, 441-450; G. Ben-Et and D. Tatarsky, *Journal of the American Oil Chemists' Society* 1972, 49(8), 499-500; G. Trapani et al., *International Journal of Pharmaceutics* 1995, 116, 95-99; and the references cited therein. Lists of surfactants and their respective HLB values have been published widely, for example in A. W. Adamson, *Physical Chemistry of Surfaces*, John Wiley and Sons, 1982.

The nonionic EO/PO block copolymer component (i.e. component (b)) of the present composition has an HLB value in the range of at least about 5. Nonionic EO/PO block copolymer components having HLB values less than about 5 typically have limited water solubility, which can be less than 5% at 20° C. Nonionic EO/PO block copolymers having HLB values near 1 are generally regarded as insoluble in water. Although nonionic EO/PO block copolymer components having HLB values less than about 5 can promote absorption of the component (a) active ingredient into propagules and developing roots, their ability to promote the desired absorption in a soil medium is observed to be significantly less than for components having HLB values of at least about 5. Typically the HLB value of component (b) is greater than 5, such as 6, 7 or 8. In certain embodiments, the HLB value of component (b) is at least about 10. Embodiments wherein the HLB value of component (b) is at least about 20 are of particular note, because nonionic EO/PO block copolymers having HLB values at least about 20 are typically very water soluble (i.e. >25% water solubility at 20° C.). High water solubility facilitates preparing highly concentrated liquid compositions from moderate amounts of water, which reduces the amount of water that needs to be evaporated after coating the propagules. Although component (b) having a high HLB value is particularly useful in the present composition, the HLB range is limited to 40. Usually component (b) has a HLB value of not more than about 35, as commercially available nonionic EO/PO block copolymers do not have an HLB value of more than about 31. Component (b) can have an HLB value of not more than about 20 or not more than about 15.

The HLB value desired for the nonionic EO/PO block copolymer component can be achieved by mixing in the proper ratio two or more nonionic EO/PO block copolymers having HLB values above and below the desired HLB value. The HLB value for a combination of surfactants is generally close to the value calculated based on HLB contributions of the constituent surfactants according to their weight percentages. Component (b) can contain a nonionic EO/PO block copolymer having a HLB value of less than 5 if component (b) also contains a sufficient amount of one or more other nonionic EO/PO block copolymers having HLB values greater than 5, so that the resulting HLB value of component (b) is at least about 5. For example, a mixture of two nonionic EO/PO block copolymers having HLB values of 1 and 15 (e.g., poloxamer 331 and poloxamer 335) in a 1:8 ratio by weight has an HLB value greater than 5. Typically the HLB value of each constituent in a mixture of nonionic EO/PO copolymers forming component (b) is at least about 5.

The nonionic EO/PO block copolymer component (b) has an average molecular weight ranging form about 1500 to about 20000 daltons. In some embodiments, the average molecular weight of component (b) is at least about 3000, 5000, 10000 or 15000 daltons. In some embodiments, the average molecular weight of component (b) is not more than about 15000 or 10000 daltons.

In the present disclosure and claims, average molecular weight of the nonionic EO/PO block copolymer component is the number average, which corresponds (for a given weight of the component) to multiplying the number of nonionic EO/PO block copolymer molecules of each molecular weight by their molecular weight, then adding the multiplication products, and finally dividing the calculated sum by the total number of nonionic EO/PO block copolymer molecules. However, other definitions of average molecular weight typically give values of similar order of magnitude. The average molecular weight of nonionic EO/PO block copolymers can be measured by methods known in the art, such as gel permeation chromatography cited by Nelson and Cosgrove, Langmuir 2005, 21, 9176-9182. Furthermore, manufacturers of nonionic EO/PO block copolymer products generally disclose average molecular weight information, which can conveniently be used to select appropriate nonionic EO/PO block copolymers for component (b) of the present composition.

Typically the molecules forming the nonionic EO/PO block copolymer component (i.e. component (b)) do not all have the same molecular weight, but instead molecular weights of the molecules form a distribution (e.g., normal Gaussian). Generally chemical synthesis processes to prepare nonionic EO/PO block copolymers give unimodal distributions of molecular weights. However, component (b) of the present composition can comprise nonionic EO/PO block copolymers prepared in different process batches from differing amounts of ethylene oxide and propylene oxide. Therefore the molecular weight distribution of component (b) can be bimodal or even multimodal. An average molecular weight of about 20000 daltons for EO/PO block copolymer molecules accommodates some molecules having considerably higher molecular weights. Typically at least about 90%, more typically at least about 95% and most typically at least about 98% of the nonionic EO/PO block copolymer molecules forming component (b) have molecular weights not exceeding about 40000 daltons.

Generally, increasing the weight ratio of component (b) to component (a) increases the absorption of component (a) into the propagule and/or developing roots to protect also the foliage of a plant grown from a propagule coated with a composition comprising components (a) and (b). However, increasing component (b) also reduces the amount of component (a) that can be included in the composition. Generally the weight ratio of component (b) to component (a) is at least about 1:10, typically at least about 1:8, more typically from at least about 1:5 or 1:4, and most typically at least about 1:3. In some embodiments the weight ratio of component (a) to component (b) is at least about 1:2 or 1:1. Generally, the weight ratio of component (b) to component (a) is not more than about 10:1, typically not more than about 8:1, more typically not more than about 5:1 or 4:1, and most typically not more than about 3:1. In some embodiments the weight ratio of component (a) to component (b) is not more than about 2:1 or 1:1.

Most generally, component (b) is from about 9 to about 91% of the composition by weight. Increasing the amount of component (b) can increase the ratio of component (b) to component (a) to facilitate absorption of component (a) from the propagule coating into the propagule and/or developing roots, but also reduces the concentration of component (a) in the coating and accordingly requires a thicker coating to provide a desired amount of component (a) for each propagule. Typically component (b) is at least about 15%, more typically at least about 20%, and most typically at least 25% of the composition by weight. In some embodiments, component (b) is at least about 30%, 35% or 40% of the composition by weight. Component (b) is typically not more than about 80%, more typically not more than about 70%, and most typically not more than about 60% of the composition by weight. In some embodiments, component (b) is not more than about 50% or 40% of the composition by weight.

Nonionic ethylene oxide-propylene oxide block copolymers include poloxamers, reverse poloxamers, poloxamines and reverse poloxamines. In poloxamers and poloxamines, the central portion of the molecule comprises one or more polyoxypropylene chains to render it lipophilic, and to the central portion are bonded at least two polyoxyethylene chains to provide the hydrophile. In poloxamers and poloxamines, the polyoxyethylene chains are terminated by primary hydroxyl groups. In reverse poloxamers and reverse poloxamines, the central portion of the molecules comprises one or more polyoxyethylene chains to provide the hydrophile, and to the central portion are bonded at least two polyoxypropylene chains to provide the lipophile (alternatively termed a hydrophobe). In reverse poloxamers and reverse poloxamines the polyoxypropylene chains are terminated by secondary hydroxyl groups.

For poloxamers and poloxamines used in component (b), the total molecular weight of the peripheral hydrophile (i.e., combination of polyoxyethylene chains) is typically in the range of about 20% to about 90% of the weight of the molecule. A hydrophile content of at least about 20% provides water solubility of at least about 5% at 20° C. A hydrophile content of at least about 60% typically provides high water solubility (i.e. >25% water solubility at 20° C.), which facilitates preparing concentrated aqueous liquid compositions. Although the hydrophile content can be 90% or even higher, more typically the total molecular weight of the hydrophile is not more than about 80% of the weight of the molecule.

For reverse poloxamers and reverse poloxamines used in component (b), the total molecular weight of the central hydrophile (i.e., polyoxyethylene chain or chains) is typically in the range of about 20% to about 90% of the weight of the molecule. However, with medium to high average total molecular weights (i.e., above about 2300 daltons) at least about 30% by weight of hydrophile is used to ensure water solubility of at least about 5% at 20° C. Although the hydrophile content can be 90% or even higher, more typically the molecular weight of the hydrophile is not more than about 80% of the weight of the molecule.

Poloxamers are of particular note, because poloxamers having an HLB value of at least about 5 have been discovered to be unexpectedly effective in promoting absorption of anthranilic diamides from a composition coating a propagule into the propagule and/or roots developing from the propagule. This enhanced absorption facilitates transport of insecticidally effective concentrations of the anthranilic diamides into developing foliage to protect against phytophagous insect pests.

The term “poloxamer” refers to a nonionic tri-block copolymer consisting of a central polyoxypropylene chain as lipophile connected at each end to polyoxyethylene chains providing the hydrophile. Poloxamers correspond to Formula 2 as shown.

$$HO(C_2H_4O)_m—(C_3H_6O)_n—(C_2H_4O)_p—H \quad 2$$

wherein m, n and p are numeric variables consistent with polymers. Suitable values of m, n and p can be easily calculated for desired total molecular weight and percent hydrophile based on the molecular weights of the subunits derived from ethylene oxide or propylene oxide.

The physical consistency of poloxamers in their pure form ranges from liquids to pastes to solids (typically described as flakes) at 20° C. Poloxamers having an HLB value of at least about 20 (or 22 when their molecular weight is less than about 3000 daltons) are typically solids at 20° C., while poloxamers having lower HLB values are typically liquids or pastes depending upon both HLB value and molecular weight (lower HLB and lower molecular weight favoring liquids versus pastes). Poloxamers that are pastes or solids facilitate component (b) functioning as an adhesive to affix the composition to a propagule. Poloxamers that are solids are of particular note as constituents of component (b), because they provide durable coatings without need to include additional adhesives such as film formers in the composition.

Lundsted U.S. Pat. No. 2,674,619 describes the preparation of poloxamers by sequential addition of propylene oxide and then ethylene oxide to propylene glycol. Because poloxamers are the products of a sequential series of reactions, the molecular weights of individual poloxamer molecules are statistical distributions about the average molecular weight. Nelson and Cosgove, *Langmuir* 2005, 21, 9176-9182 reports that some commercial poloxamer products are bimodal and may contain di-block PEO-PPO (i.e. polyoxyethylene-polyoxypropylene) as an impurity.

As described by L. E. Reeve, "The Poloxamers: Their Chemistry and Medical Applications" in *Handbook of Biodegradable Polymers*; A. J. Domb et al., Eds., Harward Academic Publishers, OPA: Amsterdam, 1997; Chapter 12, pp 232-249, a nomenclature system has been developed in which each poloxamer where m is equal to p has been assigned a number composed of three digits. This number indicates the molecular weight of the hydrophobe and the polyoxyethylene content of the respective poloxamer. The average molecular weight of the hydrophobic polyoxypropylene block is obtained by multiplying the first two digits by 100. The approximate weight percent of the polyoxyethylene is obtained by multiplying the third digit by 10. For example, poloxamer 188 is composed of a center block of polyoxypropylene having an approximate average molecular weight of about 1,800 daltons and an ethylene oxide content of approximately 80% of the total molecule. Since the number of ethylene oxide substituents in each polyoxyethylene block is statistically similar to that in the other block, poloxamer 188 should consist of a polyoxypropylene block having a molecular weight of about 1,800 daltons, flanked on either end by polyoxyethylene segments with molecular weights of about 3,600 daltons. Nominal molecular weights and polyoxyethylene to polyoxypropylene ratios vary among manufacturing lots and among suppliers.

Poloxamers are available from commercial suppliers such as BASF, which markets them under the "PLURONIC" tradename, and Croda, which markets them under the "SYNPERONIC" tradename.

As described in the "Poloxamer" article in Wikipedia (as of Jul. 8, 2009, http://en.wikipedia.org/wiki/Poloxamer), following the PLURONIC tradename, where m is equal to p, product coding starts with a letter describing its physical form at room temperature ("L" means liquid, "P" means paste, "F" means flake (solid)) followed by two or three digits. The first (left) digit (or two digits in a three-digit number) in the numerical designation multiplied by 300 indicates the approximate molecular weight of the polyoxypropylene chain, and the last digit multiplied by 10 gives the weight percentage polyoxyethylene content. For example, P103 and P104 have the same molecular weight of polyoxypropylene of about 3000 but P103 has 30 weight % and P104 has 40 weight % of polyoxyethylene.

Poloxamers useful as nonionic ethylene oxide-propylene oxide block copolymers in component (b) of the present composition typically have a central polyoxypropylene chain with an average molecular weight of at least about 900 daltons, which corresponds to the average value for the subscript variable "n" in Formula 2 being at least about 15. More typically, the average molecular weight of the central polyoxypropylene chain ranges from about 1200 daltons to about 4000 daltons.

In poloxamer molecules, the two polyoxyethylene chains together provide the hydrophile. Typically the sum of subscript variables "m" and "p" in Formula 2 is in the range from about 2 to about 300.

Examples of poloxamers suitable for component (b) of the present composition include PLURONIC F68, P85, F87, F98, P104, P105, F108, P123, and F127, corresponding to poloxamer designation of 188, 235, 237, 288, 334, 335, 338, 403, and 407.

The term "reverse poloxamer" refers to a nonionic triblock copolymer consisting of a central polyoxyethylene chain as hydrophile connected at each end to polyoxypropylene chains providing the lipophile. Reverse poloxamers correspond to Formula 3 as shown.

$$HO(C_3H_6O)_q—(C_2H_4O)_r—(C_3H_6O)_s—H \qquad 3$$

wherein q, r and s are numeric variables consistent with polymers. Suitable values of q, r and s can be easily calculated for desired total molecular weight and percent hydrophile based on the molecular weights of the subunits derived from ethylene oxide or propylene oxide.

The process of Lundsted U.S. Pat. No. 2,674,619 for preparing poloxamers can be adapted to prepare reverse poloxamers by starting with ethylene glycol instead of propylene glycol and interchanging the order of addition of ethylene oxide and propylene oxide. Reverse poloxamers are available from commercial suppliers such as BASF, which markets them under the "PLURONIC" tradename with the letter "R" inserted between the left two digits indicating (when multiplied by 100) the molecular weight of the polyoxypropylene lipophile and the right-hand digit indicating (when multiplied by 10) the weight percentage content of polyoxyethylene as hydrophile. PLURONIC product codes for reverse poloxamers omit the left-hand "L", "P" and "F" designations of physical form.

Examples of reverse poloxamers suitable for component (b) of the present composition include PLURONIC 10R5, 12R3, 17R2, 17R4, 17R8, 22R4, 25R4, 25R5, 25R8 and 31R4.

Poloxamines are structurally related to poloxamers, but as shown in Formula 4 have four chains tethered to a 1,2-diaminoethane moiety.

4 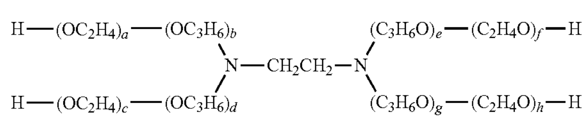 wherein a, b, c, d, e, f, g and h are numeric variables consistent with polymers. Suitable values of a, b, c, d, e, f, g and h can be easily calculated for desired total molecular weight and percent hydrophile based on the molecular weights of the subunits derived from ethylene oxide or propylene oxide.

Whereas poloxamers are prepared by sequential addition of propylene oxide then ethylene oxide to propylene glycol, poloxamines are prepared by sequential addition of propylene oxide then ethylene oxide to ethylenediamine. Poloxamines are commercially available from BASF, which markets them under the "TETRONIC" tradename. The right-hand digit of the TETRONIC number multiplied by 10 indicates the weight percentage content of polyoxyethylene as hydrophile.

Examples of poloxamines suitable for component (b) of the present composition include TETRONIC 304 and 904. Of particular note is TETRONIC 304. U.S. Patent Application Publication US 2003/0073583 discloses that TETRONIC 304 has an average molecular weight of 1650 daltons, a hydrophile content of 40% and an HLB value of 16.

Reverse poloxamines are structurally related to poloxamines but as shown in Formula 5 interchange the polyoxyethylene and polyoxypropylene chains tethered to the 1,2-diamino-ethane moiety.

5

$$H-(OC_3H_6)_b-(OC_2H_4)_a \qquad (C_2H_4O)_f-(C_3H_6O)_e-H$$
$$\diagdown N-CH_2CH_2-N \diagup$$
$$H-(OC_3H_6)_d-(OC_2H_4)_c \qquad (C_2H_4O)_h-(C_3H_6O)_g-H$$

wherein a, b, c, d, e, f, g and h are numeric variables consistent with polymers. Suitable values of a, b, c, d, e, f, g and h can be easily calculated for desired total molecular weight and percent hydrophile based on the molecular weights of the subunits derived from ethylene oxide or propylene oxide.

Whereas poloxamines are prepared by sequential addition of propylene oxide then ethylene oxide to ethylenediamine, reverse poloxamines are prepared by sequential addition of ethylene oxide then propylene oxide to ethylenediamine. Reverse poloxamines are commercially available from BASF, which markets them under the "TETRONIC" tradename with the letter "R" inserted before the right-hand digit indicating (when multiplied by 10) the weight percentage content of polyoxyethylene as hydrophile.

The physical properties of poloxamers, reverse poloxamers, poloxamines, and reverse poloxamines are well-known. Guo et al., *Journal of Colloid and Interface Science* 2006, 298, 441-450 lists average molecular weights and hydrophilic-lipophilic balance (HLB) values for PLURONIC poloxamers and PLURONIC reverse poloxamers, and also discloses a general method for calculating HLB values of poloxamers, reverse poloxamers, poloxamines, and reverse poloxamines suitable for component (b).

The present composition can optionally further comprise (c) up to about 90% by weight of one or more biologically active agents other than anthranilic diamide insecticides. Biologically active agents of component (c) do not include biocides whose principal effect is to preserve the present composition rather than protect a plant contacted with the present composition.

If present, component (c) is typically at least about 0.1% and more typically at least about 1% of the composition by weight. Typically component (c) is not more than about 60%, more typically not more than about 50%, 40% or 30%, and most typically not more than about 20% of the composition by weight. The biologically active agents forming component (c) differ from the component (a) anthranilic diamide insecticides and can include chemical compounds or biological organisms selected from the following classes: insecticides, fungicides, nematocides, bactericides, acaricides, herbicides, growth regulators such as rooting stimulants, chemosterilants, semiochemicals, repellents, attractants, pheromones and feeding stimulants (including both chemical and biological agents, and mixtures of several compounds or organisms selected from the above classes).

Compositions comprising different biologically active agents can have a broader spectrum of activity than a single agent alone. Furthermore, such mixtures can exhibit a synergistic effect.

Examples of component (c) (i.e. the one or more biologically active agents other than anthranilic diamide insecticides) are: insecticides such as abamectin, acephate, acetamiprid, acrinathrin, amidoflumet (S-1955), avermectin, azadirachtin, azinphos-methyl, bifenthrin, bifenazate, buprofezin, carbofuran, cartap, chlorfenapyr, chlorfluazuron, chlorpyrifos, chlorpyrifos-methyl, chromafenozide, clothianidin, cyflumetofen, cyfluthrin, beta-cyfluthrin, cyhalothrin, lambda-cyhalothrin, cypermethrin, cyromazine, deltamethrin, diafenthiuron, diazinon, dieldrin, diflubenzuron, dimefluthrin, dimethoate, dinotefuran, diofenolan, emamectin (including emamectin benzoate), endosulfan, esfenvalerate, ethiprole, fenothiocarb, fenoxycarb, fenpropathrin, fenvalerate, fipronil, flonicamid, flubendiamide, flucythrinate, tau-fluvalinate, flufenerim (UR-50701), flufenoxuron, fonophos, halofenozide, hexaflumuron, hydramethylnon, imidacloprid, indoxacarb, isofenphos, lufenuron, malathion, metaflumizone, metaldehyde, methamidophos, methidathion, methomyl, methoprene, methoxychlor, metofluthrin, milbemycin oxime, monocrotophos, methoxyfenozide, nicotine, nitenpyram, nithiazine, novaluron, noviflumuron (XDE-007), oxamyl, parathion, parathion-methyl, permethrin, phorate, phosalone, phosmet, phosphamidon, pirimicarb, profenofos, profluthrin, pymetrozine, pyrafluprole, pyrethrin, pyridalyl, pyrifluquinazon, pyriprole, pyriproxyfen, rotenone, ryanodine, spinetoram, spinosad, spirodiclofen, spiromesifen (BSN 2060), spirotetramat, sulprofos, tebufenozide, teflubenzuron, tefluthrin, terbufos, tetrachlorvinphos, thiacloprid, thiamethoxam, thiodicarb, thiosultap-sodium, tolfenpyrad, tralomethrin, triazamate, trichlorfon and triflumuron; and biological agents including entomopathogenic bacteria, such as *Bacillus thuringiensis* subsp. *aizawai, Bacillus thuringiensis* subsp. *kurstaki*, and the encapsulated delta-endotoxins of *Bacillus thuringiensis* (e.g., Cellcap, MPV, MPVII); entomopathogenic fungi, such as green muscardine fungus; and entomopathogenic virus including baculovirus, nucleopolyhedro virus (NPV) such as HzNPV and AfNPV, and granulosis virus (GV) such as CpGV; fungicides such as acibenzolar, aldimorph, ametoctradin, amisulbrom, azaconazole, azoxystrobin, benalaxyl, benomyl, benthiavalicarb, benthiavalicarb-isopropyl, binomial, biphenyl, bitertanol, bixafen, blasticidin-S, Bordeaux mixture (tribasic copper sulfate), boscalid/nicobifen, bromuconazole, bupirimate, buthiobate, carboxin, carpropamid, captafol, captan, carbendazim, chloroneb, chlorothalonil, chlozolinate, clotrimazole, copper oxychloride, copper salts such as copper sulfate and copper hydroxide, cyazofamid, cyflunamid, cymoxanil, cyproconazole, cyprodinil, dichlofluanid, diclocymet, diclomezine, dicloran, diethofencarb, difenoconazole, 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone, dimethomorph, dimoxystrobin, diniconazole, diniconazole-M, dinocap, discostrobin, dithianon, dodemorph, dodine, econazole, etaconazole, edifenphos, epoxiconazole, ethaboxam, ethirimol, ethridiazole, famoxadone, fenamidone, fenarimol, fenbuconazole, fencaramid, fenfuram, fenhexamide, fenoxanil, fenpiclonil, fenpropidin, fenpropimorph, fentin acetate, fentin hydroxide, ferbam, ferfurazoate, ferimzone, fluazinam, fludioxonil, flumetover, fluopicolide, fluopyram, fluoxastrobin, fluquinconazole, fluquinconazole, flusilazole, flusulfamide, flutolanil, flutriafol, folpet, fosetyl-aluminum, fuberidazole, furalaxyl, furametapyr, hexaconazole, hymexazole, guazatine, imazalil, imibenconazole, iminoctadine, iodicarb, ipconazole, iprobenfos, iprodione, iprovalicarb, isoconazole, isoprothiolane, isopyrazam, kasugamycin, kresoxim-methyl, mancozeb, mandipropamid, maneb, mapanipyrin, mefenoxam, mepronil, metalaxyl, metconazole, methasulfocarb, metiram, metominostrobin/fenominostrobin, mepanipyrim, metrafenone, miconazole, myclobutanil, neo-asozin (ferric methanearsonate), nuarimol, octhilinone, ofurace, orysastrobin, oxadixyl, oxolinic acid, oxpoconazole, oxycarboxin, paclobutrazol, penconazole, pencycuron, penflufen, penthiopyrad, perfurazoate, phosphonic acid, phthalide, picobenzamid, picoxystrobin, polyoxin, probenazole, prochloraz, procymidone, propamocarb, propamocarb-hydrochloride, propiconazole, propineb, proquinazid, prothioconazole, pyraclostrobin, pyrametostrobin, pyraoxystrobin, pyrazophos, pyrifenox, pyrimethanil, pyrifenox, pyrolnitrine, pyroquilon, quinconazole, quinoxyfen, quintozene, sedaxane, silthiofam, simeconazole, spiroxamine, streptomycin, sulfur, tebuconazole, tebufloquin, techrazene, tecloftalam, tecnazene, tetraconazole, thiabendazole, thifluzamide, thiophanate, thiophanate-methyl, thiram, tiadinil, tolclofos-methyl, tolyfluanid, triadimefon, triadimenol, triarimol, triazoxide, tridemorph, trimoprhamide tricyclazole, trifloxystrobin, triforine, triticonazole, uniconazole, validamycin, valifenalate, vinclozolin, zineb, ziram, and zoxamide; nematocides such as aldicarb, imicyafos, oxamyl and fenamiphos; bactericides such as streptomycin; and acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad.

General references for these agricultural protectants (i.e. insecticides, nematocides, acaricides and biological agents) include *The Pesticide Manual,* 13*th Edition*, C. D. S. Tomlin, Ed., British Crop Protection Council, Farnham, Surrey, U.K., 2003 and *The BioPesticide Manual, 2nd Edition*, L. G. Copping, Ed., British Crop Protection Council, Farnham, Surrey, U.K., 2001.

Of particular note are biologically active agents selected from the group consisting of the insecticides abamectin, acetamiprid, acrinathrin, avermectin, azadirachtin, azinphosmethyl, bifenthrin, buprofezin, cartap, chlorfenapyr, chlorpyrifos, clothianidin, cyfluthrin, beta-cyfluthrin, cyhalothrin, lambda-cyhalothrin, cypermethrin, cyromazine, deltamethrin, diafenthiuron, dieldrin, diflubenzuron, dimethoate, dinotefuran, emamectin benzoate, endosulfan, esfenvalerate, ethiprole, fenothiocarb, fenoxycarb, fenvalerate, fipronil, flonicamid, flubendiamide, flufenoxuron, hexaflumuron, hydramethylnon, imidacloprid, indoxacarb, lufenuron, metaflumizone, methomyl, methoxyfenozide, milbemycin oxime, nicotine, nitenpyram, nithiazine, novaluron, oxamyl, pymetrozine, pyrethrin, pyridaben, pyridalyl, pyrifluquinazon, pyriproxyfen, ryanodine, spinetoram, spinosad, spirodiclofen, spiromesifen, spirotetramat, tebufenozide, thiacloprid, thiamethoxam, thiodicarb, thiosultap-sodium, tolfenpyrad, tralomethrin, triazamate, triflumuron, *Bacillus thuringiensis* subsp. *aizawai, Bacillus thuringiensis* subsp. *kurstaki*, nucleopolyhedro virus and an encapsulated delta-endotoxin of *Bacillus thuringiensisaki*, nucleopolyhedro virus and an encapsulated delta-endotoxin of *Bacillus thuringiensis*, and the fungicides amisulbrom, azoxystrobin, bitertanol, bixafen, boscalid/nicobifen, bromuconazole, carboxin, carpropamid, captan, carbendazim, cymoxanil, cyproconazole, cyprodinil, diclocymet, difenoconazole, diniconazole, epoxiconazole, ethirimol, famoxadone, fenarimol, fenbuconazole, ferimzone, fludioxonil, fluopicolide, fluopyram, fluoxastrobin, fluquinconazole, flusilazole, flutolanil, flutriafol, hexaconazole, hymexazole, guazatine, imazalil, ipconazole, isoprothiolane, mancozeb, mefenoxam, mepronil, metalaxyl, metconazole, nuarimol, ofurace, orysastrobin, oxadixyl, oxycarboxin, paclobutrazol, penconazole, pencycuron, penflufen, penthiopyrad, perfurazoate, phthalide, picobenzamid, picoxystrobin, probenazole, prochloraz, propiconazole, proquinazid, prothioconazole, pyraclostrobin, pyrametostrobin, pyraoxystrobin, pyrimethanil, pyroquilon, quintozene, sedaxane, silthiofam, simeconazole, spiroxamine, tebuconazole, tetraconazole, thiabendazole, thifluzamide, thiophanate-methyl, thiram, tiadinil, tolclofos-methyl, triadimefon, triadimenol, triarimol, tridemorph, trifloxystrobin, triflumizole, triforine and triticonazole.

Of note is component (c) selected from biologically active agents other than biological organisms (i.e. excluding e.g., viruses, bacteria and fungi).

As an alternative to including other biologically active agents as component (c) in the present composition, other biologically active ingredients can be separately applied to propagules.

The present composition can optionally further comprise (d) up to about 80% by weight of one or more inert formulating ingredients other than nonionic EO/PO block copolymers. As used herein, the term "inert formulating ingredient" refers to ingredients included in compositions other than the chemicals or other agents providing the biological activity to control the intended pests (e.g., as described for component (c)). Such inert formulating ingredients are also known as formulation aids. When present, component (d) is typically at least 0.1% of the composition by weight. Except when the composition is intended for pelleting seeds (i.e. applying a pellet coating on seeds), the amount of component (d) is typically not more than about 20% of the composition by weight.

Component (d) can comprise a wide variety of inert formulating ingredients other than the nonionic EO/PO block copolymers of component (b), including for example, but not limitation, adhesives, liquid diluents, solid diluents, surfactants (e.g., having wetting agent, dispersant and/or anti-foam properties), antifreeze agents, preservatives such as chemical stabilizers or biocides, thickening agents and fertilizers. The nonionic EO/PO block copolymers of component (b) can function as surfactants (e.g, wetting agents, dispersants) and/or adhesives. Indeed nonionic EO/PO block copolymers are well known for their wetting and dispersing properties, although they are generally included in formulations at concentrations substantially less than specified herein. Therefore component (b) can reduce or eliminate the benefit of including certain additional inert formulating ingredients as constituents of component (d). Nevertheless, inclusion of even ingredients such as surfactants and adhesives in component (d) may still be desirable.

In the context of the present disclosure and claims, the term "adhesive" refers to a substance capable of binding component (a) to a propagule such as a seed. Adhesives include substances exhibiting tackiness such as methylcellulose or gum arabic, which are known also include substances known as film formers, which provide a durable uniform film when applied to a surface. Although an adhesive substance can always be included as a constituent of component (d) in the present composition, such inclusion is often not advantageous, because the nonionic EO/PO block copolymers of component (b) have adhesive properties. However, including additional adhesive substance is most likely to be advantageous when component (b) is a liquid or paste (i.e. not solid), and particularly when component (b) is a liquid.

The adhesive agent can comprise an adhesive polymer that may be natural or synthetic and is without phytotoxic effect on the seed to be coated. The adhesive agent can be selected from the group consisting of polyvinyl acetates, polyvinyl acetate copolymers, hydrolyzed polyvinyl acetates, polyvinylpyrrolidone-vinyl acetate copolymers, polyvinyl alcohols, polyvinyl alcohol copolymers, polyvinyl methyl ether, polyvinyl methyl ether-maleic anhydride copolymers, waxes, latex polymers, celluloses including ethylcelluloses and methylcelluloses, hydroxymethylcelluloses, hydroxypropylcelluloses, hydroxymethylpropyl-celluloses, polyvinylpyrrolidones, alginates, dextrins, malto-dextrins, polysaccharides, fats, oils, proteins, karaya gum, jaguar gum, tragacanth gum, polysaccharide gums, mucilage, gum arabics, shellacs, vinylidene chloride polymers and copolymers, soybean protein-based polymers and copolymers, lignosulfonates, acrylic copolymers, starches, polyvinylacrylates, zeins, gelatin, carboxymethylcellulose, chitosan, polyethylene oxide, acrylimide polymers and copolymers, polyhydroxyethyl acrylate, methylacrylimide monomers, alginate, ethylcellulose, polychloroprene, and syrups or mixtures thereof. The above-identified polymers include those known in the art, such as AGRIMER VA 6 and LICOWAX KST. Of note as adhesives are polyvinylpyrrolidinone-vinyl acetate copolymers and water-soluble waxes (e.g., polyethylene glycol).

The total amount of adhesive (i.e. the sum of component (b) and adhesives in component (d)) in the composition adhering to a coated propagule is generally in the range of about 0.001 to 100% of the weight of the propagule. For large seeds, the total amount of adhesive is typically in the range of about 0.05 to 5% of the seed weight; for small seeds the total amount is typically in the range of about 1 to 100%, but can be greater than 100% of seed weight if the seed is pelleted (i.e. a pellet coating is applied to the seed). For other propagules the total amount of adhesive is typically in the range of 0.001 to 2% of the propagule weight.

Optionally, the present composition can contain up to about 10% (based on the weight of the composition) of liquid diluents as a constituent of component (d). In the context of the present disclosure and claims, the term "liquid diluent" excludes water unless otherwise indicated. When the present composition comprises one or more liquid diluents, they generally amount to at least 0.1% of the composition by weight. Typically as a constituent in a composition coating a propagule, the liquid diluents are relatively nonvolatile, i.e. have a normal boiling point of greater than about 100° C., more typically greater than about 160° C., and preferably greater than about 200° C. Examples of liquid diluents include N-alkyl-pyrrolidones, dimethyl sulfoxide, ethylene glycol, polypropylene glycol, propylene carbonate, dibasic esters, paraffins, alkylnaphthalenes, oils of olive, castor, linseed, tung, sesame, corn, peanut, cottonseed, soybean, rapeseed and coconut, fatty acid esters, ketones such as isophorone and 4-hydroxy-4-methyl-2-pentanone, and alcohols such as cyclohexanol, decanol, benzyl and tetrahydrofurfuryl alcohol. Typical liquid diluents are described in Marsden, *Solvents Guide*, 2nd Ed., Interscience, New York, 1950. As the presence of liquid diluents can soften a composition coating a propagule, the present composition typically comprises not more than about 5% of liquid diluents by weight.

Optionally, the present composition can contain up to about 75% (based on the weight of the composition) of solid diluents as a constituent of component (d). When the present composition comprises one or more solid diluents, they generally amount to at least about 0.01%, more typically at least about 0.1% of the composition by weight. In the context of the present disclosure and claims, solid diluents are considered to be solid substances principally providing bulk instead of other useful (e.g., adhesive, surfactant) properties. Typical solid diluents are described in Watkins et al., *Handbook of Insecticide Dust Diluents and Carriers*, 2nd Ed., Dorland Books, Caldwell, N.J. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. High concentrations of solid diluents (i.e. up to about 75%) are typically included in a composition of the present invention for pelleting seeds. For pelleting seeds, the solid diluents are preferably insoluble, for example, bentonite, montmorillonite, attapulgite and kaolin (clays), silica (e.g., powdered silica) and calcium carbonate (e.g., ground limestone). When the present composition is not intended for use in pelleting seeds, the amount of solid diluents is typically not more than about 10% of the composition by weight.

The nonionic EO/PO block copolymers of component (b) typically obviate the need to include additional surfactants such as wetting agents and dispersants, but one or more such surfactants can be included in the composition as a constituent of component (d). If the present composition includes additional wetting agents or dispersants, they typically are present in an amount of at least about 0.1% of the composition by weight. Typically the present composition does not include more than about 15%, more typically not more than about 10%, and most typically not more than about 5% of additional surfactants by weight.

Examples of dispersing agents include anionic surfactants such as phosphate esters of tristyrylphenol ethoxylates (e.g., SOPROPHOR 3D33), alkylarylsulfonic acids and their salts (e.g., SUPRAGIL MNS90), lignin sulfonates (e.g., ammonium lignosulfonate or sodium lignosulfonate), polyphenol sulfonates, polyacrylic acids, acrylic graft copolymers such as acrylic acid/methyl methacrylate/polyoxyethylene graft copolymers (e.g., ATLOX 4913), and other polymers combining polyoxyalkylene with acid functionality such as ATLOX 4912 (block copolymer of polyoxyethylene and hydroxystearic acid).

Examples of wetting agents (some of which overlap with dispersing agents) include alkyl sulfate salts (e.g., SIPON LC 98 (sodium lauryl sulfate)), alkyl ether sulfate salts (e.g., sodium lauryl ether sulfate), alkylarylsulfonates (i.e. salts of alkylarylsulfonic acids, including arylsulfonic acids substituted with more than one alkyl moiety) such as sodium or calcium alkylbenzenesulfonates (e.g., RHODACAL DS1) and alkylnaphthalenesulfonates (e.g., RHODACAL BX-78), α-olefin sulfonate salts, dialkyl sulfosuccinate salts and salts of polycarboxylic acids.

Additional surfactants include, for example, ethoxylated alcohols, ethoxylated alkylphenols, ethoxylated sorbitan fatty acid esters, ethoxylated sorbitol fatty acid esters, ethoxylated amines, ethoxylated fatty acids and esters (including ethoxylated vegetable oils), organosilicones, N,N-dialkyltaurates, glycol esters, formaldehyde condensates, and block polymers other than nonionic ethylene oxide-propylene oxide block copolymers.

Component (d) can also comprise one or more anti-foaming agents. Anti-foaming agents are surfactants that can effectively either prevent foam formation or reduce or eliminate it once it has formed. Examples of anti-foaming agents include silicone oils, mineral oils, polydialkylsiloxanes such as polydimethylsiloxanes, fatty acids and their salts with polyvalent cations such as calcium, magnesium and aluminum, alkyne diols (e.g., SURFYNOL 104), and fluoroaliphatic esters, perfluoroalkylphosphonic and perfluoro-alkylphosphinic acids, and salts thereof. When the present composition comprises one or more anti-foaming agents, they typically amount to at least about 0.01% and not more than about 3% of the composition by weight. More typically, anti-foaming agents are not more than about 2% and most typically not more than about 1% of the composition by weight.

*McCutcheon's Emulsifiers and Detergents and McCutcheon's Functional Materials* (*North America and International Editions*, 2001), The Manufacturing Confection Publ. Co., Glen Rock, N.J., as well as Sisely and Wood, *Encyclopedia of Surface Active Agents*, Chemical Publ. Co., Inc., New York, 1964, list surfactants and recommended uses.

Component (d) can comprise one or more antifreeze agents. Antifreeze agents prevent freezing of the composition of the present invention extended with an aqueous liquid carrier before coating on propagules. Examples of antifreeze agents, which may overlap with liquid diluents, include glycols such as ethylene glycol, diethylene glycol, propylene glycol, dipropylene glycol, glycerol, 1,3-propanediol, 1,2-propanediol or polyethylene glycol of molecular weight in the range from about 200 to about 1000 daltons. Antifreeze agents of note for the composition of the present invention include ethylene glycol, propylene glycol, glycerol, 1,3-propanediol and 1,2-propanediol. When component (d) comprises one or more antifreeze agents, they typically amount to at least about 0.1% and not more than about 14% of the composition by weight. More typically, antifreeze agents do not amount to more than 10% and most typically not more than about 8% of the total weight of the composition.

Component (d) can comprise one or more thickening agents. Thickening agents (i.e. thickeners) increase viscosity of the continuous liquid medium formed when the present composition is extended with an aqueous liquid carrier. By increasing viscosity, the propensity of solid particles (e.g., of component (a)) to settle is reduced. Because component (b) also increases viscosity, including one or more thickening agents in component (d) is generally not necessary and indeed can be unhelpful if the viscosity of the composition is already as much as desired. Including one or more thickening agents in component (d) can be beneficial for slowing settling of particles of component (a) if the composition is extended with a large amount of aqueous liquid carrier relative to component (b), particularly when component (b) comprises mainly nonionic EO/PO block copolymers of relatively low molecular weight (i.e less than about 3500 daltons). Examples of thickening agents useful for the present composition include polyols such as glycerol, polysaccharides including heteropolysaccharides such as xanthan gum, and hydrated clays with very small particle sizes (e.g., 2 nm) such as the hydrated magnesium aluminosilicate ACTI-GEL 208 (Active Minerals). Glycerol is of note as having both antifreeze and thickener properties. An extensive list of thickeners and their applications can be found in *McCutcheon's* 2005, *Volume* 2: *Functional Materials* published by MC Publishing Company. If component (d) comprises one or more thickening agents, they typically amount to at least about 0.1% and not greater than about 5% of the composition by weight.

Component (d) can comprise a preservative constituent consisting essentially of one or more stabilizing agents or biocides, the amount of the preservative constituent is typically up to about 1% of the composition by weight. When a preservative constituent is present, it typically amounts to at least about 0.01% of the composition by weight. The preservative constituent does not exceed typically about 1%, more typically about 0.5% and most typically about 0.3% of the total weight of the composition.

Stabilizing agents can prevent decomposition of active ingredients (i.e. component (a) and/or component (c)) during storage, for example, anti-oxidants (such as butylhydroxytoluene) or pH modifiers (such as citric acid or acetic acid). Biocides can prevent or reduce microbial contamination within a formulated composition. Particularly suitable biocides are bactericides such as LEGEND MK (mixture of 5-chloro-2-methyl-3(2H)-isothiazolone with 2-methyl-3(2H)-isothiazolone), EDTA (ethylenediaminetetraacetic acid), formaldehyde, benzoic acid, or 1,2-benzisothiazol-3(2H)-one or its salts, e.g., PROXEL BD or PROXEL GXL (Arch). Of note is the present composition wherein component (d) comprises a biocide, in particular, a bactericide such as 1,2-benzisothiazol-3(2H)-one or one of its salts.

Component (d) can also comprise one or more fertilizers. Fertilizers included in component (d) can provide plant nutrients such as nitrogen, phosphorus and potassium and/or micronutrients such as manganese, iron, zinc and molybdenum. Of note for inclusion in component (d) are micronutrients such as manganese, iron, zinc and molybdenum. If one of more fertilizers are present, they typically amount to at least about 0.1% and not more than about 20% of the composition by weight, although greater amounts can be included.

Other formulation ingredients can be included in the present composition as component (d) such as rheology modifiers, dyes, and the like. These ingredients are known to one skilled in the art and can be found described, for example, in *McCutcheon's, Volume* 2*: Functional Materials* published by MC Publishing Company annually.

One aspect of the present invention is a geotropic propagule coated with an insecticidally effective amount of the aforedescribed composition. Geotropic propagules include seeds. The present invention is applicable to virtually all seeds, including seeds of wheat (*Triticum aestivum* L.), durum wheat (*Triticum durum* Desf.), barley (*Hordeum vulgare* L.), oat (*Avena sativa* L.), rye (*Secale cereale* L.), maize (*Zea mays* L.), sorghum (*Sorghum vulgare* Pers.), rice (*Oryza sativa* L.), wild rice (*Zizania aquatica* L.), cotton (*Gossypium barbadense* L. and *G. hirsutum* L.), flax (*Linum usitatissimum* L.), sunflower (*Helianthus annuus* L.), soybean (*Glycine max* Merr.), garden bean (*Phaseolus vulgaris* L.), lima bean (*Phaseolus limensis* Macf.), broad bean (*Vicia faba* L.), garden pea (*Pisum sativum* L.), peanut (*Arachis hypogaea* L.), alfalfa (*Medicago sativa* L.), beet (*Beta vulgaris* L.), garden lettuce (*Lactuca sativa* L.), rapeseed (*Brassica rapa* L. and *B. napus* L.), cole crops such as cabbage, cauliflower and broccoli (*Brassica oleracea* L.), turnip (*Brassica rapa* L.), leaf (oriental) mustard (*Brassica juncea* Coss.), black mustard (*Brassica nigra* Koch), tomato (*Lycopersicon esculentum* Mill.), potato (*Solanum tuberosum* L.), pepper (*Capsicum frutescens* L.), eggplant (*Solanum melongena* L.), tobacco (*Nicotiana tabacum*), cucumber (*Cucumis sativus* L.), muskmelon (*Cucumis melo* L.), watermelon (*Citrullus vulgaris* Schrad.), squash (*Curcurbita pepo* L., *C. moschata* Duchesne. and *C. maxima* Duchesne.), carrot (*Daucus carota* L.), zinnia (*Zinnia elegans* Jacq.), cosmos (e.g., *Cosmos bipinnatus* Cay.), chrysanthemum (*Chrysanthemum* spp.), sweet scabious (*Scabiosa atropurpurea* L.), snapdragon (*An-*

*tirrhinum majus* L.), gerbera (*Gerbera jamesonii* Bolus), baby's-breath (*Gypsophila paniculata* L., *G. repens* L. and *G. elegans* Bieb.), statice (e.g., *Limonium sinuatum* Mill., *L. sinense* Kuntze.), blazing star (e.g., *Liatris spicata* Willd., *L. pycnostachya* Michx., *L. scariosa* Willd.), lisianthus (e.g., *Eustoma grandiflorum* (Raf.) Shinn), yarrow (e.g., *Achillea filipendulina* Lam., *A. millefolium* L.), marigold (e.g., *Tagetes patula* L., *T. erecta* L.), pansy (e.g., *Viola cornuta* L., *V. tricolor* L.), impatiens (e.g., *Impatiens balsamina* L.), petunia (*Petunia* spp.), geranium (*Geranium* spp.) and coleus (e.g., *Solenostemon scutellarioides* (L.) Codd). Geotropic propagules also include rhizomes, tubers, bulbs or corms, or viable divisions thereof. Suitable rhizomes, tubers, bulbs and corms, or viable divisions thereof include those of potato (*Solanum tuberosum* L.), sweet potato (*Ipomoea batatas* L.), yam (*Dioscorea cayenensis* Lam. and *D. rotundata* Poir.), garden onion (e.g., *Allium cepa* L.), tulip (*Tulipa* spp.), gladiolus (*Gladiolus* spp.), lily (*Lilium* spp.), narcissus (*Narcissus* spp.), dahlia (e.g., *Dahlia pinnata* Cay.), iris (*Iris germanica* L. and other species), crocus (*Crocus* spp.), anemone (*Anemone* spp.), hyacinth (*Hyacinth* spp.), grape-hyacinth (*Muscari* spp.), freesia (e.g., *Freesia refracta* Klatt., *F. armstrongii* W. Wats), ornamental onion (*Allium* spp.), woodsorrel (*Oxalis* spp.), squill (*Scilla peruviana* L. and other species), cyclamen (*Cyclamen persicum* Mill. and other species), glory-of-the-snow (*Chionodoxa luciliae* Boiss. and other species), striped squill (*Puschkinia scilloides* Adams), calla lily (*Zantedeschia aethiopica* Spreng., *Z. elliottiana* Engler and other species), gloxinia (*Sinnigia speciosa* Benth. & Hook.) and tuberous begonia (*Begonia tuberhybrida* Voss.). The above recited cereal, vegetable, ornamental (including flower) and fruit crops are illustrative, and should not be considered limiting in any way. For reasons of insect control spectrum and economic importance, embodiments coating seeds of cotton, maize, soybean, rapeseed and rice, and coating tubers and bulbs of potato, sweet potato, garden onion, tulip, daffodil, crocus and hyacinth are of note. Also of note are embodiments wherein the geotropic propagule is a seed, for example, of cotton, maize, soybean, rapeseed or rice.

The present composition can be coated on geotropic propagules that contain genetic material introduced by genetic engineering (i.e. transgenic) or modified by mutagenesis to provide advantageous traits. Examples of such traits include tolerance to herbicides, resistance to phytophagous pests (e.g., insects, mites, aphids, spiders, nematodes, snails, plant-pathogenic fungi, bacteria and viruses), improved plant growth, increased tolerance of adverse growing conditions such as high or low temperatures, low or high soil moisture, and high salinity, increased flowering or fruiting, greater harvest yields, more rapid maturation, higher quality and/or nutritional value of the harvested product, or improved storage or process properties of the harvested products. Transgenic plants can be modified to express multiple traits. Examples of plants containing traits provided by genetic engineering or mutagenesis include varieties of corn, cotton, soybean and potato expressing an insecticidal *Bacillus thuringiensis* toxin such as YIELD GARD, KNOCKOUT, STARLINK, BOLLGARD, NuCOTN and NEWLEAF, and herbicide-tolerant varieties of corn, cotton, soybean and rapeseed such as ROUNDUP READY, LIBERTY LINK, IMI, STS and CLEARFIELD, as well as crops expressing N-acetyltransferase (GAT) to provide resistance to glyphosate herbicide, or crops containing the HRA gene providing resistance to herbicides inhibiting acetolactate synthase (ALS). The present insecticidal composition may interact synergistically with traits introduced by genetic engineering or modified by mutagenesis, thus enhancing phenotypic expression or effectiveness of the traits or increasing the insect control effectiveness of the present composition. In particular, the present insecticidal composition may interact synergistically with the phenotypic expression of proteins or other natural products toxic to invertebrate pests to provide greater-than-additive control of these pests.

The thickness of coatings of the present composition on geotropic propagules can vary from thin films 0.001 mm thick to layers about 0.5 to 5 mm thick. Generally, a coating that increases the weight of a seed up to 25% is defined as a film coating. Film-coated seed retains the shape and the general size of the uncoated seed. A coating that increases the weight of the seed more than 25% is referred to as a pellet coating. Typically a pellet coating increases seed weight by at least about 100%. A process for applying a pellet coating to a seed is referred to as pelleting. Coatings on geotropic propagules can comprise more than one adhering layer, only one of which need comprise the present composition. Generally pellets are more satisfactory for small seeds, because their ability to provide an insecticidally effective amount of the present composition is not limited by the surface area of the seed, and pelleting small seeds also facilitates seed transfer and planting operations. Because of their larger size and surface area, large seeds and bulbs, tubers, corms and rhizomes and their viable cuttings are generally not pelleted, but instead coated with a thin film.

For application of a coating of the aforedescribed composition to a geotropic propagule, the composition is typically first extended with a volatile aqueous liquid carrier to provide a liquid composition consisting of about 5 to 80 weight % of the aforedescribed (unextended) composition (i.e. mixture comprising components (a), (b) and optionally (c) and (d)) and about 20 to 95 weight % of the volatile aqueous liquid carrier. Alternatively and more typically, one or more of the composition components is first mixed with the volatile aqueous liquid carrier before the components are combined to provide the liquid composition containing components (a), (b) and optionally (c) and (d) in combination with about 20-95 weight % of the volatile aqueous liquid carrier. The amount of volatile aqueous liquid carrier is more typically at least about 25% and most typically at least about 30% of the liquid composition by weight. Also, the amount of volatile aqueous liquid carrier is more typically not more than about 70% of the liquid composition by weight.

In the context of present disclosure and claims, the expression "volatile aqueous liquid carrier" refers a composition consisting of at least about 50% water by weight and optionally one or more water-soluble compounds that are liquid at 20° C. and have a normal boiling point of not greater than about 100° C. These water-soluble liquid compounds should be nonphytotoxic to the geotropic propagule to be coated. Examples of such water-soluble liquid compounds are acetone, methyl acetate, methanol and ethanol. However, a volatile aqueous liquid carrier mostly or entirely of water is typically preferable, because water is inexpensive, nonflammable, environmentally friendly and nonphytotoxic. Typically the volatile aqueous liquid carrier comprises at least about 80%, more typically at least about 90%, and most typically at least about 95% water by weight. In some embodiments, the volatile aqueous liquid carrier consists essentially of water. In some embodiments, the volatile liquid carrier is water.

In the liquid composition comprising the volatile aqueous liquid carrier, the volatile aqueous liquid carrier forms a continuous liquid phase in which other components (e.g., components (a), (b) and optionally (c) and (d)) are suspended or dissolved. Note that because the liquid composition consists of a volatile aqueous liquid carrier together with an insecticidal composition defined using the open-ended term "comprising", the insecticidal composition can introduce unspecified liquid or solid constituents into the liquid composition. Furthermore, components (b), (c) and (d) can include liquid constituents (e.g., relatively nonvolatile liquid diluents, antifreeze agents) that can dissolve in and become part of the continuous liquid phase. Typically at least some of component (a) is present as particles suspended in the continuous liquid phase and therefore the liquid composition can be described as a suspension concentrate composition. In some embodiments at least about 90%, or 95% or 98% of component (a) is present as particles suspended in the continuous liquid phase. Typically more than 95% by weight of the particles have a particle size less than about 10 µm.

The aggregation state of the nonionic EO/PO block copolymer component (i.e. component (b)) in the liquid composition depends on such parameters as ingredients, concentration, temperature and ionic strength. The liquid composition typically comprises suspended particles of component (a) having large surface areas relative to their volumes. Nonionic EO/PO block copolymer molecules are generally adsorbed to such interfaces (e.g., as monolayers, bilayers or hemimicelles) in preference to remaining in solution, and only when the interfaces are saturated do high concentrations of the molecules remain in the aqueous phase. Therefore the presence of particles of component (a) allows the liquid composition to accommodate more component (b) without forming a separate component (b) phase than would be expected based solely on water solubility. If the liquid composition contains component (b) in excess of both its adsorption onto component (a) particles and its solubility in the aqueous carrier phase, a portion of component (b) will be present in a discrete phase, either as solid particles or as liquid droplets depending upon the physical properties (e.g., melting point) of component (b).

The liquid composition comprising the volatile aqueous liquid carrier is often most conveniently prepared by mixing components (a) and (b) and optionally (c) and (d) with the volatile aqueous liquid carrier (e.g., water). As noted above, component (b) is water-soluble to the extent of at least 5% at 20° C. For ease of dissolution of component (b) in the formulation, it is preferred to dissolve component (b) in the aqueous liquid carrier prior to mixing with the other ingredients.

In the liquid composition, the median particle size of particles of component (a) is preferably less than about 10 µm to provide good suspensibility as well as high biological availability and coating coverage of the propagule. More preferably the median particle size of component (a) is less than 4 µm or 3 µm or 2 µm and most preferably less than about 1 µm. Typically the median particle size is at least about 0.1 µm, but smaller particle sizes are suitable.

Milling can be used to reduce the particle size of component (a) as well as other solid components. Milling methods are well-known and include ball-milling, bead-milling, sand-milling, colloid milling and air-milling. These can be combined with high-speed blending, which typically involves high shear, to prepare suspensions and dispersions of particles. Of particular note is ball- or bead-milling for reducing the particle size of component (a). Other components, such as component (b), can be included in the mixture for milling or later mixed with the milled mixture. However, other components comprising solid particles initially having a particle size of greater than 10 µm and low water solubility are typically included in the mixture for milling. Although nonionic EO/PO block copolymer component (b) and optional additional surfactant of component (d) can be added after milling component (a), typically a portion of component (b) and/or optional additional surfactant is included in the mixture to facilitate milling component (a) to small particle size (i.e. less than 10 µm).

Milling is often unneeded in methods for preparing the liquid composition by first dissolving component (a) in an organic solvent. In one method, components (a) and (b) and optionally other components are dissolved in an organic solvent, and then a miscible solvent in which components (a) and (b) are much less soluble is added to the solution of components (a) and (b) to form a precipitate. The precipitate is collected and suspended in the volatile aqueous liquid carrier (e.g., water) for coating propagules. N-methyl-2-pyrrolidone and diethyl ether are suitable as the more soluble and less soluble solvents, respectively, when the nonionic EO/PO block copolymers of component (b) have a high polyoxyethylene content (e.g., about 80% or greater), thus causing low solubility in diethyl ether.

In a related method, components (a) and (b) and optionally other components are dissolved in an organic solvent system comprising a lower boiling solvent in which component (a) is very soluble and a higher boiling solvent in which component (a) is less soluble (e.g., a binary solvent system of dichloromethane and ethanol), and then the solvent is evaporated under vacuum. The residue is then suspended in the volatile aqueous liquid carrier (e.g., water) for coating propagules.

In another method, component (a) and component (b) are dissolved in a water-miscible organic solvent such as N-methyl-2-pyrrolidone. The solution is then placed inside a sealed dialysis membrane, which is selected to allow the organic solvent and water to equilibrate but not allow passage of component (a) and component (b). The sealed dialysis membrane is then placed in water to allow replacement of the organic solvent with water. Water entering the dialysis membrane causes component (a) to crystallize and form a slurry. The resultant aqueous slurry is used to coat propagules.

After the liquid composition comprising the volatile aqueous liquid carrier has been prepared, it can be applied to the surface of a propagule by any of several techniques known in the art, which involve evaporating the volatile aqueous liquid carrier to leave a coating of the insecticidal composition comprising components (a), (b) and optionally (c) and (d) adhering to the surface of the propagule. Various coating machines and processes are available to one skilled in the art. Suitable processes include those listed in P. Kosters et al., Seed Treatment Progress and Prospects, 1994 BCPC Monograph No. 57 and the references listed therein. Coating processes are also described in U.S. Pat. Nos. 5,527,760 and 6,202,345. Three well-known techniques include the use of drum coaters, fluidized bed techniques and spouted beds. Seeds can be pre-sized prior to coating. After coating, the seeds are dried and then optionally sized by transfer to a sizing machine. These machines are known in the art.

In one method, propagules are coated by spraying the liquid composition comprising the volatile aqueous liquid carrier directly into a tumbling bed of propagules and then drying the propagules. In an embodiment for coating seeds, the seed and coating material are mixed in a conventional seed coating apparatus. The optimal rate of rolling and application of coating depends upon the seed. For large oblong seeds such as that of cotton, a satisfactory seed coating apparatus comprises a rotating type pan with lifting vanes turned at sufficient rotational speed to maintain a rolling action of the seed, facilitating uniform coverage. The seed coating should be applied over sufficient time to allow drying to minimize clumping of the seed. Using forced air or heated forced air can allow increasing the rate of application. One skilled in the art will also recognize that this process may be a batch or continuous process. As the name implies, a continuous process allows the seeds to flow continuously throughout the product run. New seeds enter the pan in a steady stream to replace coated seeds exiting the pan.

One embodiment of seed coating is seed pelleting. The pelleting process typically increases the seed weight from 2 to 100 times and can be used to also improve the shape of the seed for use in mechanical seeders. Pelleting compositions generally contain a solid diluent, which is typically an insoluble particulate material, such as clay, ground limestone, powdered silica, etc. to provide bulk in addition to a filmformer or sticking agent. Depending on the extent of coating applied, pelletizing may provide a spherical shape to the seeds which are normally elongated or irregularly shaped. A method for producing pellets is described in Agrow, *The Seed Treatment Market*, Chapter 3, PJB Publications Ltd., 1994.

One aspect of the present invention is a method for protecting a geotropic propagule and plant derived therefrom from a phytophagous insect pest by coating the propagule with an insecticidally effective amount of the liquid composition comprising components (a), (b) and optionally (c) and (d) along with a volatile aqueous liquid carrier and then evaporating the volatile aqueous liquid carrier of the composition. This coating process constitutes a treatment of the propagule by providing a coating of an insecticidally effective amount of the insecticidal composition on the propagule. The coating of the composition on the propagule provides an insecticidally effective amount of component (a) (i.e. one or more anthranilic diamide insecticides) available for absorption into the propagule and/or roots developing from the propagule. The nonionic EO/PO block copolymer of component (b) has been discovered to remarkably increase the absorption of component (a) into the propagules and/or developing roots to provide through xylem transport an insecticidally effective concentration of component (a) in even foliage developing from the coated propagule. Sufficiently increasing the absorption can raise concentrations of component (a) above the minimum concentration for insecticidal effectiveness in not only the lower foliage but also middle to upper foliage, and provide protection later into the growing season. Insecticidally effective concentrations of component (a) protect the propagule and derived plant from injury or damage caused by a phytophagous insect pest by controlling the insect pest. This control can include killing the insect pest, interfering with its growth, development or reproduction, and/or inhibiting its feeding. Typically control involves feeding inhibition and death of the insect pest.

Generally to protect a seed and foliage developing therefrom from a phytophagous insect pest, the present composition is coated on a geotropic propagule to provide component (a) in an amount ranging from about 0.001 to 50% of the weight of the propagule; for seeds the amount is more often in the range of about 0.01 to 50% of the seed weight, and most typically for large seeds in the range of about 0.01 to 10% of the seed weight. However, larger amounts up to about 100% or more are useful, particularly for pelleting small seed for extended invertebrate pest control protection. For propagules such as bulbs, tubers, corms and rhizomes and their viable cuttings, generally the amount of component (a) included in the composition coating ranges from about 0.001 to 5% of the propagule weight, with the higher percentages used for smaller propagules. One skilled in the art can easily determine the insecticidally effective amount of the present composition and component (a) necessary for the desired level of phytophagous insect pest control and seed and plant protection.

As referred to in this disclosure, the term "phytophagous insect pest" includes larvae of the order Lepidoptera, such as armyworms, cutworms, loopers, and heliothines in the family Noctuidae (e.g., fall armyworm (*Spodoptera fugiperda* J. E. Smith), beet armyworm (*Spodoptera exigua* Hübner), black cutworm (*Agrotis ipsilon* Hufnagel), cabbage looper (*Trichoplusia ni* Hübner), tobacco budworm (*Heliothis virescens* Fabricius)); borers, casebearers, webworms, coneworms, cabbageworms and skeletonizers from the family Pyralidae (e.g., European corn borer (*Ostrinia nubilalis* Hübner), navel orangeworm (*Amyelois transitella* Walker), corn root webworm (*Crambus caliginosellus* Clemens), sod webworm (*Herpetogramma licarsisalis* Walker)); leafrollers, budworms, seed worms, and fruit worms in the family Tortricidae (e.g., codling moth (*Cydia pomonella* L. (L. means Linnaeus)), grape berry moth (*Endopiza viteana* Clemens), oriental fruit moth (*Grapholita molesta* Busck)); and many other economically important lepidoptera (e.g., diamondback moth (*Plutella xylostella* L. of family Plutellidae), pink bollworm (*Pectinophora gossypiella* Saunders of family Gelechiidae), gypsy moth (*Lymantria dispar* L. of family Lymantriidae)); foliar feeding larvae and adults of the order Coleoptera including weevils from the families Anthribidae, Bruchidae, and Curculionidae (e.g., boll weevil (*Anthonomus grandis* Boheman), rice water weevil (*Lissorhoptrus oryzophilus* Kuschel), rice weevil (*Sitophilus oryzae* L.)); flea beetles, cucumber beetles, rootworms, leaf beetles, potato beetles, and leafminers in the family Chrysomelidae (e.g., Colorado potato beetle (*Leptinotarsa decemlineata* Say), western corn rootworm (*Diabrotica virgifera* virgifera LeConte)); chafers and other beetles from the family Scaribaeidae (e.g., Japanese beetle (*Popillia japonica* Newman) and European chafer (*Rhizotrogus majalis* Razoumowsky)); wireworms from the family Elateridae and bark beetles from the family Scolytidae; adults and larvae of the order Dermaptera including earwigs from the family Forficulidae (e.g., European earwig (*Forficula auricularia* L.), black earwig (*Chelisoches morio* Fabricius)); adults and nymphs of the orders Hemiptera and Homoptera such as, plant bugs from the family Miridae, cicadas from the family Cicadidae, leafhoppers (e.g. *Empoasca* spp.) from the family Cicadellidae, planthoppers from the families Fulgoroidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Coccidae, Diaspididae and Margarodidae, lace bugs from the family Tingidae, stink bugs from the family Pentatomidae, cinch bugs (e.g., *Blissus* spp.) and other seed bugs from the family Lygaeidae, spittlebugs from the family Cercopidae squash bugs from the family Coreidae, and red bugs and cotton stainers from the family Pyrrhocoridae; adults and immatures of the order Orthoptera including grasshoppers, locusts and crickets (e.g., migratory grasshoppers (e.g., *Melanoplus sanguinipes* Fabricius, *M. differentialis* Thomas), American grasshoppers (e.g., *Schistocerca americana* Drury), desert locust (*Schistocerca gregaria* Forskal), migratory locust (*Locusta migratoria* L.), mole crickets (*Gryllotalpa* spp.)); adults and immatures of the order Diptera including leafminers, midges, fruit flies (Tephritidae), frit flies (e.g., *Oscinella frit* L.), soil maggots and other Nematocera; adults and immatures of the order Thysanoptera including onion thrips (*Thrips tabaci* Lindeman) and other foliar feeding thrips. Of note is the present method for protecting a propagule or plant derived therefrom from a phytophagous insect pest wherein the insect pest is in a taxonomic order selected from Hemiptera (particularly the families Aleyrodidae, Aphidadae, Cicadellidae, Delphacidae) and Lepidoptera (particularly the families Gelechiidae, Lymantriidae, Noctuidae, Plutellidae, Pyralidae and Torticidae). Of particular note is the present method wherein the insect pest is in the family Noctuidae.

Without further elaboration, it is believed that one skilled in the art using the preceding description can utilize the present invention to its fullest extent. The following Examples are, therefore, to be construed as merely illustrative and not limiting of the disclosure in any way whatsoever.

EXAMPLES

Table 1 describes the nonionic EO/PO block copolymers used in the Examples and Comparative Examples. All these EO/PO block copolymers are products of BASF Corporation. Molecular weight and HLB values for poloxamers are from Guo et al., *Journal of Colloid and Interface Science* 2006, 298, 441-450.

TABLE 1

Identity of Nonionic EO/PO Block Copolymers

| Tradename | Common Name | MW (daltons) | HLB |
|---|---|---|---|
| PLURONIC F68 | Poloxamer 188 | 8400 | 29 |
| PLURONIC F87 | Poloxamer 237 | 7700 | 24 |
| PLURONIC F98 | Poloxamer 288 | 13000 | 28 |
| PLURONIC F108 | Poloxamer 338 | 14600 | 27 |
| PLURONIC F127 | Poloxamer 407 | 12600 | 22 |
| PLURONIC L101 | Poloxamer 331 | 3800 | 1 |
| PLURONIC L121 | Poloxamer 401 | 4400 | 1 |
| PLURONIC P85 | Poloxamer 235 | 4600 | 16 |
| PLURONIC P104 | Poloxamer 334 | 5900 | 13 |
| PLURONIC P105 | Poloxamer 335 | 6500 | 15 |
| PLURONIC P123 | Poloxamer 403 | 5750 | 8 |

Table 2 describes other ingredients used in the Examples and Comparative Examples.

TABLE 2

Identity of Other Ingredients

| Name | Identity |
|---|---|
| Compound 1 | 3-Bromo-1-(3-chloro-2-pyridinyl)-N-[4-cyano-2-methyl-6-[(methylamino)carbonyl]phenyl]-1H-pyrazole-5-carboxamide |
| Compound 2 | 3-Bromo-N-[4-chloro-2-methyl-6-[(methylamino)carbonyl]phenyl]-1-(3-chloro-2-pyridinyl)-1H-pyrazole-5-carboxamide |
| AGNIQUE GLY 96 (Cognis Corp) | Glycerol |
| RHODOPOL 23 (Rhodia) | Xanthan gum (Heteropolysaccharide) |
| LEGEND MK (Rohm & Haas) | Mixture of 5-chloro-2-methyl-thiazol-3-one and 2-methylthiazol-3-one |
| DOW 2-3101 | 20% Silicone emulsion in water |
| ACTI-GEL 208 (Active Minerals) | Hydrous magnesium aluminosilicate |

PCT Patent Publication WO 2006/062978 discloses methods for preparing 3-bromo-1-(3-chloro-2-pyridinyl)-N-[4-cyano-2-methyl-6-[(methylamino)carbonyl]phenyl]-1H-pyrazole-5-carboxamide (i.e., Compound 1). Example 15 of this publication discloses preparation of Compound 1 as a powder melting at 177-181° C. (with apparent decomposition), which is a polymorph crystal form that is readily hydrated. Example 15 also discloses recrystallization from 1-propanol to provide crystals melting at 217-219° C., which is an anhydrous polymorph crystal form that is resistant to hydration. The samples of Compound 1 used in the present Examples and Comparative Examples were assayed to contain about 94-98% by weight of Compound 1, which is believed to be a mixture of these two polymorph crystal forms.

PCT Patent Publication WO 03/015519 also discloses methods for preparing 3-bromo-N-[4-chloro-2-methyl-6-[(methylamino)carbonyl]phenyl]-1-(3-chloro-2-pyridinyl)-1H-pyrazole-5-carboxamide (i.e. Compound 2). Example 7 of this publication discloses preparation of Compound 2 as a powder melting at 239-240° C. The samples of Compound 2 used in the present Examples and Comparative Examples were assayed to contain about 96-97% by weight of Compound 2.

The weight percentages of Compound 1 or 2 reported in the present Examples refer to the amount of Compound 1 or 2 contained in the technical material used; the other constituents in the technical material are not separately listed, but when added to weight percentages of the listed composition components result in a total of about 100%.

General Procedure for Coating Seeds

A fluidized bed system was used for coating seeds with the compositions described in the following examples. Seeds were tossed by vertical streams of hot air while being sprayed with the aqueous composition. The hot air evaporated the water carrier from the composition applied to the seeds. The amount of composition introduced into the coating system was adjusted to compensate for material lost exiting the coater or coating areas other than the seeds, so as to deliver the stated target application rate of active ingredients (e.g., Compound 1 or Compound 2) to the seeds.

General Procedure for Assaying Anthranilic Diamide Concentration in Leaves

Plant leaves were macerated using a Geno/Grinder 2000 bead beater homogenizer (SPEX CertiPrep, Metuchen, N.J., USA), and then acetonitrile (~5 mL/g of leaf tissue) was added. The mixture was further shaken for 1 minute using the Geno/Grinder homogenizer, and then centrifuged. The acetonitrile extract supernatant was analyzed by high performance liquid chromatography with tandem mass spectrometry detection (HPLC/MS/MS) using a Waters (Milford, Mass. USA) Alliance HT2795 chromatograph and Zorbax SB C18 (2.1×50 mm, 5 μm) column eluted with mixtures of water and acetonitrile containing 0.1% (volume/volume) of formic acid, with detection by a Waters Quattro Micro API Mass Spectrometer using electrospray ionization (ESI+). Standard solutions of Compound 1 and Compound 2 were prepared by adding measured amounts of stock solutions of Compound 1 or Compound 2 in acetonitrile or tetrahydrofuran to acetonitrile extracts of leaves from plants grown from untreated seeds.

In a laboratory test involving 2nd instar larvae of *Spodoptera frugiperda* on maize leaves, a concentration of 0.033 μg of Compound 2 per g of leaf tissue resulted in 50% mortality within 72 h, and a concentration of 0.037 μg per g of tissue was needed to achieve 100% mortality within 72 h. In an additional laboratory test involving 2nd instar larvae of *Spodoptera frugiperda* on soybean leaves treated with various concentrations of Compound 1 or Compound 2, the concentration of Compound 1 needed to achieve 50% mortality within 96 h was found to be about 4-5 times greater than the concentration of Compound 2.

Examples 1-6 and Comparative Example A

Aqueous compositions comprising Compound 1 and a PLURONIC nonionic EO/PO block copolymer were prepared from the relative amounts of ingredients listed in Table 3. For each Example composition, the PLURONIC compound was dissolved in water, the aqueous solution was added to the other ingredients, and then the resulting mixture was milled. Median particle size for the compositions of Examples 1-6 was measured using a Malvern Mastersizer instrument.

TABLE 3

Identity and weight percentage of ingredients in aqueous
compositions of Examples 1-6 and Comparative Example A

| INGREDIENTS | EXAMPLES | | | | | | |
| --- | --- | --- | --- | --- | --- | --- | --- |
| | 1 | 2 | 3 | 4 | 5 | 6 | Comparative A |
| PLURONIC Identity | F68 | F87 | F98 | F108 | F108 | F127 | F108 |
| Weight percentage | 23.3 | 20.7 | 12.5 | 10.2 | 13.7 | 12.4 | 3.0 |
| Compound 1 | 23.3 | 20.7 | 41.8 | 34.0 | 13.7 | 12.4 | 49.8 |
| ACTI-GEL 208 | 0.5 | 0.5 | 0.5 | 0.5 | 0.5 | 0.5 | 0.5 |
| RHODOPOL 23 | 0.2 | 0.2 | 0.2 | 0.2 | 0.2 | 0.2 | 0.2 |
| DOW 2-3101 | 0.3 | 0.3 | 0.3 | 0.05 | 0.05 | 0.05 | 0.3 |
| AGNIQUE GLY 96 | 3 | 3 | 3 | 3 | 3 | 3 | 3 |
| Propylene glycol | 1.5 | 1.5 | 1.5 | 1.5 | 1.5 | 1.5 | 1.5 |
| Water | 46.6 | 51.8 | 37.6 | 49.5 | 66.3 | 68.8 | 38.5 |
| Median particle size (μm) | 0.75 | 0.52 | 0.44 | 0.82 | 0.82 | 0.77 | — |

The compositions of Examples 1-6 and Comparative Examples A were mixed with (1A) a 1:3 by weight mixture of the fungicide products MAXIM 4FS (40.3% fludioxonil) and APRON XL (33.3% mefenoxam), and (2) the colorant Acid Blue Dye, and then the resultant compositions were used to coat canola seeds at an application rate of 0.6 g of Compound 1, 0.067 mL of the fungicide mixture (1A) and 0.033 g of the colorant (2) per 100 g of seeds (100 g corresponding to about 23,400 seeds for Examples 1, 5 and 6, and 25,640 seeds for Examples 2-4 and Comparative Example A). ("Canola" is a cultivar of the rapeseed species Brassica napus L. that produces an edible oil.)

The coated canola seeds were then evaluated for ability to provide Compound 1 to leaves developing from the seeds. Each treatment involved four pots to provide quadruple replication. Four coated canola seeds were planted in sterile Matapeake sand blend soil in each pot and then grown in a growth chamber (25° C., 18 h light, 6 h dark) for 18-20 days. Three plants in each pot were selected for sampling. From each of the three plants, the second leaf was cut at the stem. All three leaves collected from each pot were placed into one vial and then analyzed according to the general procedure described above for assaying anthranilic diamide concentration in leaves. The concentrations measured from leaves in each of the four pots (total of 12 leaves) were averaged to provide the values reported in Table 4.

TABLE 4

Concentration of Compound 1 in the second leaves of canola plants
grown from seeds coated with compositions of Examples 1-6 and
Comparative Example A.

| EXAMPLE | EO/PO copolymer | Ratio of EO/PO copolymer to Compound 1 | μg Compound 1/g of leaf |
| --- | --- | --- | --- |
| 1 | PLURONIC F68 | 1:1 | 0.09 |
| 2 | PLURONIC F87 | 1:1 | 0.17 |
| 3 | PLURONIC F98 | 1:3.3 | 0.19 |
| 4 | PLURONIC F108 | 1:3.3 | 0.09 |
| 5 | PLURONIC F108 | 1:1 | 0.08 |
| 6 | PLURONIC F127 | 1:1 | 0.06 |
| Comparative A | PLURONIC F108 | 1:16.6 | 0.03 |

The results for Comparative Example A show that a ratio of 1:16.6 of component (b) to component (a) resulted in minimal concentrations of Compound 1 in the second leaf.

A caged insect study was conducted using canola seeds coated according to Examples 1 and 2. Seeds were planted individually (i.e. one seed per pot) in pots that were 2 cm wide and 4 cm deep and filled with a commercial potting mix (LA 4 Sunshine Mix®, SunGro Horticulture, Vancouver, Canada, comprising Canadian sphagnum peat moss, coarse grade perlite, gypsum, dolomitic lime, and a long-lasting wetting agent) After 7 days, when the plants had reached the cotyledon stage, each of 16 potted plants grown from seeds coated with a particular treatment (i.e. Example 1 or Example 2) was infested with 2 adult flea beetles (Phyllotreta cruciferae Goeze) and placed together in a cage. Therefore the cage contained a total of 32 beetles. Four days after placing the plants with beetles in the cage, the number of dead beetles was recorded and the percent mortality was calculated. Mortality of beetles placed with plants grown from canola seeds coated with the compositions of Examples 1 and 2 was 20% and 62%, respectively, corrected using Abbott's formula adjusting for control group mortality (W. S. Abbott, J. Econ. Entomol. 1925, 18, 265-267).

Examples 7-12

Examples 7-12 illustrate further methods for preparing compositions comprising Compound 1 and a nonionic EO/PO block copolymer. Compound 1 used in Examples 7-9 was in the form of a fine powder. The compositions described in Examples 7-12 were mixed with (1A) a 1:3 by weight mixture of the fungicide products MAXIM 4FS (40.3% fludioxonil) and APRON XL (33.3% mefenoxam), and (2) the colorant Acid Blue Dye, and then the resultant compositions were used to coat canola seeds at an application rate of 0.6 g of Compound 1, 0.067 mL of the fungicide mixture (1A) and 0.033 g of the colorant (2) per 100 g of seeds (100 g corresponding to about 23,400 seeds). The coated seeds were planted and grown in a growth chamber, and the second leaves were analyzed as described for Examples 1-6.

Example 7

Compound 1 (2 g) was added to a solution of PLURONIC F108 (2 g) dissolved in water (14 g). The mixture was placed in an ultrasonic bath for 250 minutes, then stirred for 16 days, and finally allowed to stand for 14 days. The resultant composition was mixed with the fungicide mixture (1A) and colorant (2), and used to coat canola seeds, which were planted, and the second leaves were analyzed as described above. Analysis showed a concentration of 0.24 μg Compound 1/g canola leaf.

Example 8

PLURONIC F108 (10.0 g) was dissolved in water (80 g). A portion of this solution (12.0 g) was combined with Compound 1 (5.0 g), thus providing about a 1:3.75 weight ratio of PLURONIC F108 to Compound 1. The mixture was stirred for 18 days and then allowed to stand for 4 days. The resultant composition was mixed with the fungicide mixture (1A) and colorant (2), and used to coat canola seeds, which were planted, and the second leaves were analyzed as described above. Analysis showed a concentration of 0.12 µg Compound 1/g canola leaf.

Example 9

A portion (1.91 g) of the aqueous PLURONIC F108 solution of Example 8 was mixed with Compound 1 (0.702 g), thus providing about a 1:3.3 weight ratio of PLURONIC F108 to Compound 1. This composition was mixed for only about a minute before being further mixed with the fungicide mixture (1A) and colorant (2), and used to coat canola seeds, which were planted, and the second leaves were analyzed as described above. Analysis showed a concentration of 0.12 µg Compound 1/g canola leaf.

Example 10

Compound 1 (2.8 g) and PLURONIC P85 (0.90 g) were dissolved in 70 mL of a solution consisting of 30 wt % ethanol and 70 wt % dichloromethane. The solvent was removed by rotary evaporation. The residue was mixed with water and then the fungicide mixture (1A) and colorant (2), and used to coat canola seeds, which were planted, and the second leaves were analyzed as described above. Analysis showed a concentration of 0.12 µg Compound 1/g canola leaf.

Example 11

Compound 1 (2 g) and PLURONIC F68 (2 g) were dissolved in N-methyl-2-pyrrolidone (10 mL). This solution was added to diethyl ether (200 mL), resulting in the formation of a solid precipitate. The solid was collected, washed with diethyl ether, and dried. The solid was suspended in water, and the suspension was mixed with the fungicide mixture (1A) and colorant (2), and used to coat canola seeds, which were planted, and the second leaves were analyzed as described above. Analysis showed a concentration of 0.12 µg Compound 1/g canola leaf.

Example 12

Compound 1 (3.00 g) and PLURONIC P85 (3.00 g) were dissolved in N-methyl-2-pyrrolidinone (15 mL). The solution was transferred into cellulosic dialysis tubing (about 1000 dalton molecular weight cut off, 14 cm length). The ends of the tubing were clamped to retain the contents for dialysis. The tubing was immersed in de-ionized water (about 3.8 L), which was changed 3 times over 3 days. The resultant aqueous slurry was mixed with the fungicide mixture (1A) and colorant (2), and used to coat canola seeds, which were planted, and the second leaves were analyzed as described above. Analysis showed a concentration of 0.28 µg Compound 1/g canola leaf.

Example 13

The composition of Example 1 was mixed with (1B) a 1.2:3 by weight mixture of the fungicide products MAXIM 4FS and APRON XL, and (2) the colorant Acid Blue Dye, and then the resultant composition was used to coat maize seeds at an application rate of 0.11 g of Compound 1, 0.02 mL of the fungicide mixture (1B) and 0.05 g of the colorant (2) per 100 g of seeds (100 g corresponding to about 442 seeds). This treatment provided an average of about 0.25 mg of each of Compound 1 and PLURONIC F68 per seed.

The coated maize seeds were then evaluated for ability to provide Compound 1 to leaves developing from the seeds. Each treatment involved at least 5 pots to provide replication. Four coated maize seeds were planted in sterile Matapeake sand blend soil in each pot and then grown in a growth chamber (25° C., 16 h light, 8 h dark) for 13-14 days. Three plants in each pot were selected for sampling. From each of the three plants, the third leaf was cut at the stalk. All three leaves collected from each pot were placed into one vial and then analyzed according to the general procedure described above for assaying anthranilic diamide concentration in leaves. The concentrations measured from leaves in each of the replicated pots (total of at least 15 leaves) were averaged to provide a value of 0.7 µg Compound 1/g maize leaf.

Example 14

The composition of Example 3 was mixed with the fungicide mixture (1B) and colorant (2), and used to coat maize seeds, which were planted, and the third leaves were analyzed as described in Example 13. This treatment provided an average of about 0.25 mg of Compound 1 and 0.075 mg of PLURONIC F98 per seed. Analysis of the third leaves showed a concentration of 1.0 µg Compound 1/g maize leaf.

Example 15

A composition containing 10 wt % PLURONIC F108, 33.6 wt % Compound 1, 48.8 wt % water, 0.5 wt % ACTI-GEL 208, 0.2 wt % RHODOPOL 23, 0.3 wt % DOW 2-3101, 0.05 wt % LEGEND MK, 1.5 wt % propylene glycol, and 3 wt % AGNIQUE GLY 96 was prepared according to the method of Examples 1-6. The median particle size was measured to be 0.56 µm. This composition was mixed with the fungicide mixture (1B) and colorant (2), and used to coat maize seeds, which were planted, and the third leaves were analyzed as described in Example 13. This treatment provided an average of about 0.25 mg of Compound 1 and 0.074 mg of PLURONIC F108 per seed. Analysis of the third leaves showed a concentration of 1.0 µg Compound 1/g maize leaf.

Examples 16-20

Aqueous compositions comprising Compound 2 and a PLURONIC nonionic EO/PO block copolymer were prepared from the relative amounts of ingredients listed in Table 3. For each Example composition, the PLURONIC compound was dissolved in water, the aqueous solution was added to the other ingredients, and then the resulting mixture was milled. Median particle size for the compositions of Examples 18 and 19 was measured using a Malvern Mastersizer instrument.

TABLE 5

Identity and weight percentage of ingredients in aqueous compositions of Examples 16-20

| INGREDIENTS | EXAMPLES | | | | |
| --- | --- | --- | --- | --- | --- |
| | 16 | 17 | 18 | 19 | 20 |
| PLURONIC Identity | F68 | F87 | F98 | F108 | F127 |
| Weight percentage | 14.6 | 13.6 | 12.7 | 10.2 | 9.5 |

TABLE 5-continued

Identity and weight percentage of ingredients in aqueous compositions of Examples 16-20

| INGREDIENTS | EXAMPLES | | | | |
|---|---|---|---|---|---|
| | 16 | 17 | 18 | 19 | 20 |
| Compound 2 | 48.8 | 45.3 | 42.3 | 33.9 | 31.5 |
| ACTI-GEL 208 | 0.5 | 0.5 | 0.5 | 0.5 | 0.5 |
| RHODOPOL 23 | 0.2 | 0.2 | 0.2 | 0.2 | 0.2 |
| DOW 2-3101 | 0.3 | 0.3 | 0.3 | 0.05 | 0.05 |
| AGNIQUE GLY 96 | 3 | 3 | 3 | 3 | 3 |
| Propylene glycol | 1.5 | 1.5 | 1.5 | 1.5 | 1.5 |
| Water | 29.3 | 34.0 | 38.0 | 49.2 | 52.4 |
| Median particle size (μm) | — | — | 0.60 | 0.56 | — |

The compositions of Examples 16-20 were mixed with (1B) a 1.2:3 weight mixture of the fungicide products MAXIM F4S and APRON XL, and (2) the colorant Acid Blue Dye, and then the resultant compositions were used to coat maize seeds at an application rate of 0.11 g of Compound 2, 0.02 mL of the fungicide mixture (1B) and 0.05 g of the colorant (2) per 100 g of seeds (100 g corresponding to about 442 seeds). This treatment provided an average of about 0.25 mg of Compound 2 per seed. The coated maize seeds were planted and grown in a growth chamber as described for Example 13. After 13-14 days from seeding, the third leaves were excised from the stalks of three maize plants and combined in the same vial for analysis.

Also, the compositions of Examples 18 and 19 were mixed with the fungicide mixture (1B) and colorant (2), and then the resultant compositions were used to coat maize seeds at an application rate of 0.22 g of Compound 2, 0.027 mL of the fungicide mixture (1B) and 0.033 g of colorant (2) per 100 g of seeds. This treatment provided an average of about 0.50 mg of Compound 2 per seed. The coated maize seeds were planted outdoors in a field in rows 76 cm wide with a seed spacing of 20 cm. A preemergence herbicide was applied immediately after planting in the soil. After 13-14 days from seeding, the third leaves were excised from the stalks of three maize plants and combined in the same vial for analysis. In the field tests, each test unit consisting of the third leaves from three plants was replicated at least five times (i.e. at least 15 third leaves were analyzed).

The third leaves from the growth chamber and field test maize plants were analyzed using the method described above, and the measured concentrations are listed in Table 6.

TABLE 6

Concentration of Compound 2 in the third leaves of maize plants grown from seeds coated with compositions of Examples 16-20.

| EXAMPLE | EO/PO copolymer | Ratio of EO/PO copolymer to Compound 1 | μg Compound 2/g of leaf | |
|---|---|---|---|---|
| | | | Growth Chamber | Field Test |
| 16 | PLURONIC F68 | 1:3.3 | 0.18 | — |
| 17 | PLURONIC F87 | 1:3.3 | 0.18 | — |
| 18 | PLURONIC F98 | 1:3.3 | 0.20 | 0.10 |
| 19 | PLURONIC F108 | 1:3.3 | 0.17 | 0.09 |
| 20 | PLURONIC F127 | 1:3.3 | 0.19 | — |

Examples 21-23 and Comparative Examples B and C

Aqueous compositions comprising Compound 2 and a PLURONIC nonionic EO/PO block copolymer were prepared by first mixing the PLURONIC (25 g) with water (75 g), and then mixing a portion of the aqueous PLURONIC mixture (20 g) with Compound 2 (5 g) in the form of a powder. The median particle size in the compositions of Examples 21, 22 and 23 was measured to be 0.84, 0.86 and 0.80 μm, respectively. The compositions of Examples 21-23 and Comparative Examples A and B were mixed with (1B) a 1.2:3 weight mixture of the fungicide products MAXIM F4S and APRON XL, and (2) the colorant Acid Blue Dye, and then the resultant compositions were used to coat maize seeds at an application rate of 0.11 g of Compound 2, 0.02 mL of the fungicide mixture (1B) and 0.05 g of the colorant (2) per 100 g of seeds (100 g corresponding to about 442 seeds). This treatment provided an average of about 0.25 mg of Compound 2 per seed. The coated maize seeds were planted in at least 5 pots containing 4 seeds per pot, and grown in a growth chamber as described for Example 13. After 13-14 days from seeding, from each pot the third leaves were excised from the stalks of three maize plants and combined in the same vial for analysis.

Also, the compositions of Examples 21-23 were mixed with the fungicide mixture (1B) and colorant (2), and then the resultant compositions were used to coat maize seeds at an application rate of 0.22 g of Compound 2, 0.027 mL of the fungicide mixture (1B) and 0.033 g of colorant (2) per 100 g of seeds. This treatment provided an average of about 0.50 mg of Compound 2 per seed. The maize seeds coated for the field tests were moist, so powdered mica (obtained through Kwizda Agro, about 0.19 g per 100 g of seed) was applied as an overcoat. The coated maize seeds were planted outdoors in a field in rows 76 cm wide with a seed spacing of 20 cm. A preemergence herbicide was applied immediately after planting in the soil. After 13-14 days from seeding, the third leaves were excised from the stalks of three maize plants and combined in the same vial for analysis. In the field tests, each test unit consisting of third leaves from three plants was replicated at least five times.

The third leaves from the growth chamber and field test maize plants were analyzed using the method described above, and the measured concentrations are listed in Table 7.

TABLE 7

Concentration of Compound 2 in the third leaves of maize plants grown from seeds coated with compositions of Examples 21-23 and Comparative Examples B and C.

| EXAMPLE | EO/PO copolymer | Ratio of EO/PO copolymer to Compound 2 | μg Compound 2/g of leaf | |
|---|---|---|---|---|
| | | | Growth Chamber | Field Test |
| 21 | PLURONIC P104 | 1:1 | 0.30 | 0.08 |
| 22 | PLURONIC P105 | 1:1 | 0.26 | 0.09 |
| 23 | PLURONIC P123 | 1:1 | 0.24 | 0.21 |
| Comparative B | PLURONIC L101 | 1:1 | 0.09 | — |
| Comparative C | PLURONIC L121 | 1:1 | 0.07 | — |

The results for Comparative Examples B and C show that substitution of a nonionic EO/PO block copolymer with an HLB value of 1 (compared to at least about 5 required for the present invention) that is insoluble in water (compared to at least about 5% water solubility at 20° C. required for the present invention) resulted in diminished concentrations of Compound 2 in the third leaves of maize plants.

After 28 days from seeding, the sixth leaf of the test plants grown in the field from maize seeds coated according to Examples 22 and 23 was excised for a bioassay with fall armyworm (*Spodoptera frugiperda* J.E. Smith). For each treatment (i.e. Example 22 or 23), twelve pieces (3.8-cm long) were cut from the excised sixth leaves and each piece was individually placed with one second-instar larva in a container, which was then set in a growth chamber (25° C., 16 h light, 8 h dark). Larval mortality was recorded after 4 days. Mortality of larvae placed with leaf pieces grown from maize seeds coated with the compositions of Examples 22 and 23 was 50 and 58%, respectively, compared to 4% for a control group of larvae placed with leaf pieces grown from seeds not treated with anthranilic diamide insecticides.

What is claimed is:

1. An insecticidal composition comprising by weight based on the total weight of the composition:
(a) from about 9 to about 91% of one or more anthranilic diamide insecticides selected from Formula 1, N-oxides, and salts thereof,

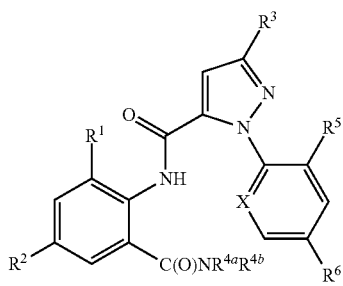

wherein
X is N;
$R^1$ is $CH_3$, Cl, Br or F;
$R^2$ is H, F, Cl, Br or —CN;
$R^3$ is F, Cl, Br, $C_1$-$C_4$ haloalkyl or $C_1$-$C_4$ haloalkoxy;
$R^{4a}$ is H, $C_1$-$C_4$ alkyl, cyclopropylmethyl or 1-cyclopropylethyl;
$R^{4b}$ is H or $CH_3$;
$R^5$ is H, F, Cl or Br; and
$R^6$ is H, F, Cl or Br; and
(b) from about 9 to about 91% of a nonionic ethylene oxide-propylene oxide block copolymer component selected from poloxamers, reverse poloxamers, poloxamines and reverse poloxamines, having a water solubility of at least about 5% by weight at 20° C., a hydrophilic-lipophilic balance value of at least or about 5 and an average molecular weight ranging from about 3000 to about 20000 daltons;
wherein the ratio of component (b) to component (a) is about 1:5 to about 10:1 by weight.

2. The composition of claim 1 wherein component (a) is selected from compounds of Formula 1 wherein $R^1$ is $CH_3$; $R^2$ is Cl or —CN; $R^3$ is Br; $R^{4a}$ is $CH_3$; $R^{4b}$ is H; $R^5$ is Cl; and $R^6$ is H; and salts thereof.

3. The composition of claim 2 wherein component (a) is the compound of Formula 1 wherein $R^2$ is Cl.

4. The composition of claim 2 wherein component (a) is the compound of Formula 1 wherein $R^2$ is —CN.

5. The composition of claim 1 wherein component (b) is at least or about 15% of the composition by weight.

6. The composition of claim 1 wherein component (b) is selected from poloxamers and poloxamines.

7. The composition of claim 6 wherein component (b) is selected from poloxamers.

8. The composition of claim 1 further comprising at least one fungicide or insecticide other than anthranilic diamide insecticides.

9. A geotropic propagule coated with an insecticidally effective amount of the composition of claim 1.

10. The geotropic propagule of claim 9 which is a seed.

11. The geotropic propagule of claim 10 wherein the seed is a seed of cotton, maize, soybean, rapeseed or rice.

12. A liquid composition consisting of about 5 to 80 weight % of the composition of claim 1 and about 20 to 95 weight % of a volatile aqueous liquid carrier.

13. A method for protecting a geotropic propagule and plant derived therefrom from a phytophagous insect pest, the method comprising coating the propagule with an insecticidally effective amount of the liquid composition of claim 12 and then evaporating the volatile aqueous liquid carrier of the composition.

14. The method of claim 13 wherein the insect pest is in a taxonomic order selected from Hemiptera and Lepidoptera.

15. The composition of claim 1 wherein the ratio of component (b) to component (a) is at least or about 1:4 by weight.

* * * * *